US012653793B2

(12) United States Patent
Cruz et al.

(10) Patent No.: US 12,653,793 B2
(45) Date of Patent: Jun. 16, 2026

(54) TELLURIUM NANOSTRUCTURES WITH ANTIMICROBIAL AND ANTICANCER PROPERTIES SYNTHESIZED BY ALOE VERA-MEDIATED GREEN CHEMISTRY

(71) Applicant: Northeastern University, Boston, MA (US)

(72) Inventors: David Medina Cruz, Jamaica Plain, MA (US); Ada Vernet Crua, Brighton, MA (US); Thomas J. Webster, Barrington, RI (US)

(73) Assignee: Northeastern University, Boston, MA (US)

( * ) Notice: Subject to any disclaimer, the term of this patent is extended or adjusted under 35 U.S.C. 154(b) by 989 days.

(21) Appl. No.: 17/417,446

(22) PCT Filed: Jan. 6, 2020

(86) PCT No.: PCT/US2020/012436
§ 371 (c)(1),
(2) Date: Jun. 23, 2021

(87) PCT Pub. No.: WO2020/142790
PCT Pub. Date: Jul. 9, 2020

(65) Prior Publication Data
US 2022/0071919 A1     Mar. 10, 2022

Related U.S. Application Data

(60) Provisional application No. 62/788,422, filed on Jan. 4, 2019.

(51) Int. Cl.
| | |
|---|---|
| *A61K 9/51* | (2006.01) |
| *A61K 33/04* | (2006.01) |
| *A61K 36/886* | (2006.01) |
| *B82Y 5/00* | (2011.01) |
| *B82Y 40/00* | (2011.01) |

(52) U.S. Cl.
CPC .......... *A61K 9/5192* (2013.01); *A61K 9/5176* (2013.01); *A61K 33/04* (2013.01); *A61K 36/886* (2013.01); *B82Y 5/00* (2013.01); *B82Y 40/00* (2013.01)

(58) Field of Classification Search
CPC .... A61K 9/5192; A61K 9/5176; A61K 33/04; A61K 36/886; A61K 9/51; B82Y 5/00; B82Y 40/00; A61P 31/04; A61P 35/00
See application file for complete search history.

(56) References Cited

U.S. PATENT DOCUMENTS

2012/0282185 A1    11/2012  Dobson et al.

OTHER PUBLICATIONS

Elsoud et al. (Synthesis and investigations on tellurium myconanoparticles, Biotechnology Reports, 2018 (Year: 2018).*
Tippayawat et al. (Green synthesis of silver nanoparticles in aloe vera plant extract prepared by a hydrothermal method and their synergistic antibacterial activity. PeerJ, 2016) (Year: 2016).*
Lin et al. (Antibacterial Activities of Tellurium Nanomaterials, Chem. Asian J. 2012 (Year: 2012).*
Oh et al. (Rapid green synthesis of silver nanoparticles from *Chrysanthemum indicum* L and its antibacterial and cytotoxic effects: an in vitro study. Int. J. of Nanomedicine. 2014 (Year: 2014).*
Brown (Synthesis and characterization of PVP-coated tellurium nanorods and their antibacterial and anticancer properties, J Nanopart Res, 2018 (Year: 2018).*
Balaji et al., "Microwave-assisted fibrous decoration of mPE surface utilizing Aloe vera extract for tissue engineering applications", International Journal of Nanomedicine, 2015: 10, pp. 5909-5923.
Brown et al., "Synthesis and characterization of PVP-coated tellurium nanorods and their antibacterial and anticancer properties", Journal of Nanoparticle Research, (2018) vol. 20, Issue 9, article id. 254. 13 pages.
Hunyadi et al., "Enhanced growth of tellurium nanowires under conditions of macromolecular crowding", Phys. Chem. Chem. Phys., 2017,19, pp. 16477-16484.
Zhang, Bohan, "Preparation of Nanoparticles By Green Synthesis and a Study on Their Antibacterial and Anticancer Properties", Northeastern University, Mar. 16, 2019 [retrieved on Feb. 14, 2020], Retrieved from the Internet .semanticscholar.org/paper/Preparation-Of-Nanoparticles-By-Green-Synthesis-And-Zhang/ 2c6b80df95f796ba028af189a9e435dd72017abc pp. 65-91.
Iravani et al., "Synthesis of silver nanoparticles: chemical, physical and biological methods", Research in Pharmaceutical Sciences. 2014, pp. 385-406.
Zhang et al., "Silver Nanoparticles: Synthesis, Characterization, Properties, Applications, and Therapeutic Approaches", International Journal of Molecular Sciences. 2016;17(9): 1534; 34 pages.
Cruz et al., "Synthesis and characterization of biogenic selenium nanoparticles with antimicrobial properties made by *Staphylococcus aureus*, methicillin-resistant *Staphylococcus aureus* (MRSA), *Escherichia coli*, and Pseudomonas aeruginosa", J Biomed Mater Res A. May 2018; 106(5):1400-1412.
Jiang et al., "Facile Synthesis and Optical Properties of Small Selenium Nanocrystals and Nanorods", Nanoscale Research Letters 12 (2017): 401; 6 pages.
Wadhwani et al., "Green Synthesis of Selenium Nanoparticles Using *Acinetobacter* Sp. SW30: Optimization, Characterization and its Anticancer Activity in Breast Cancer Cells", International Journal of Nanomedicine 12 (2017), pp. 6841-6855.
(Continued)

*Primary Examiner* — Robert A Wax
*Assistant Examiner* — John Seungjai Kwon
(74) *Attorney, Agent, or Firm* — Adams & Reese LLP

(57) ABSTRACT

Tellurium (Te) nanostructures are synthesized using green aloe vera chemistry methods, and the synthesized Te nanostructures provide methods of inhibiting bacterial cells and cancer cells without cytotoxicity towards normal cells. The aloe vera chemistry methods for synthesizing Te nanostructures do not produce toxic byproducts and do not require toxic reagents in comparison to traditional chemical synthetic methods for making Te nanostructures.

7 Claims, 22 Drawing Sheets

(56)                    References Cited

OTHER PUBLICATIONS

Pugin et al., Pugin, Benoit et al. "Glutathione Reductase-Mediated Synthesis of Tellurium-Containing Nanostructures Exhibiting Antibacterial Properties", Applied and Environmental Microbiology 80.22 (2014): pp. 7061-7070.

Liu et al., "Understanding the Solvent Molecules Induced Spontaneous Growth of Uncapped Tellurium Nanoparticles", Scientific Reports 6 (2016): 32631; 10 pages.

Turner et al., "Microbial processing of tellurium as a tool in biotechnology", Biotechnol. Adv. 2012; 30(5):954-963.

Fernandez-Lodeiro et al., "Synthesis and Characterization of PtTe2 Multi-Crystallite Nanoparticles using Organotellurium Nanocomposites", Scientific Reports. 2017;7:9889; 10 pages.

Lu et al., "A Green Chemical Approach to the Synthesis of Tellurium Nanowires", Langmuir 2005, 21, pp. 6002-6005.

Gomez-Graria et al., "Biogenic Synthesis of Metal Nanoparticles Using a Biosurfactant Extracted from Corn and Their Antimicrobial Properties", Nanomaterials 2017;7(6):139; 14 pages.

Ollivier et al., "Volatilization and Precipitation of Tellurium by Aerobic, Tellurite-Resistant Marine Microbes", Applied and Environmental Microbiology. 2008; 74(23): pp. 7163-7173.

Yadav et al., "Characterization and Antibacterial Activity of Synthesized Silver and Iron Nanoparticles using Aloe vera", J Nanomed Nanotechnol (2016) 7:384; 7 pages.

Chandran et al., "Synthesis of goldnanotriangles and silver nanoparticles using Aloevera plant extract" Biotechnology Progress (2006) 22: pp. 577-583.

Nejatzadeh-Barandozi, "Antibacterial Activities and Antioxidant Capacity of Aloe Vera", Organic and Medicinal Chemistry Letters 3 (2013): 5; 8 pages.

Logaranjan et al., "Shape- and Size-Controlled Synthesis of Silver Nanoparticles Using Aloe Vera Plant Extract and Their Antimicrobial Activity." Nanoscale Research Letters 11 (2016): 520; 9 pages.

Zare et al., "Biosynthesis and recovery of rod-shaped tellurium nanoparticles and their bactericidal activities", Mater Res Bull. 2012;47(11):3719-3725.

Shakibaie et al., "Antimicrobial and Antioxidant Activity of the Biologically Synthesized Tellurium Nanorods; A Preliminary In vitro Study", Iranian J Biotech. Oct. 2017;15(4):e1580; pp. 268-276.

Guisbiers et al., "Synthesis of tunable tellurium nanoparticles", Semicond. Sci. Technol. (2017), 32 04LT0; 5 pages.

Guihua et al., "Solvothermal synthesis of polycrystalline tellurium nanoplates and their conversion into single crystalline nanorods", RSC Adv., 2014, 4, 954; pp. 954-958.

* cited by examiner

TELLURIUM NANOSTRUCTURES WITH ANTIMICROBIAL AND ANTICANCER PROPERTIES SYNTHESIZED BY ALOE VERA-MEDIATED GREEN CHEMISTRY

CROSS-REFERENCE TO RELATED APPLICATIONS

This application claims priority to U.S. Provisional Application No. 62/788,422, filed 4 Jan. 2019, the entirety of which is incorporated herein by reference.

BACKGROUND

Bacterial resistance to antibiotics has emerged as an increasing threat to health [1] due to the misuse of antibiotics and the development of bacterial strains with resistance. Data from the Centers for Disease Control indicate that at least 2 million people become infected with antibiotic-resistant bacteria in the United States annually, and of those, at least 23,000 die as a consequence. Therefore, novel approaches to combat antibacterial resistance to antibiotics need to be developed, especially those that do not require the use of antibiotics.

Nanotechnology provides an alternative solution with the implementation of nanomaterials [2]. Nanoparticles are highly reactive due to a high surface-to-volume ratio, and can penetrate biofilms. Moreover, many synthetic approaches allow for tunability of nanoparticle characteristics, such as coatings and functionalization, for enhanced penetration of these biofilms. Nanoparticles have also been shown to decrease bacterial survival rate without being highly toxic to mammalian cells [3].

Some commonly used materials for nanoparticle synthesis include silver [4, 5, 6], gold [7, 8, 9], titanium dioxide [10], zinc oxide [11], silica [12], carbon [13], selenium [14, 15, 16] and tellurium [17, 18]. Tellurium (Te) is considered a rare and mildly-toxic metalloid, belonging to the chalcogen family, which also includes sulfur, selenium, and polonium [19]. In nature, tellurium can be found in different oxidation states: tellurate ($TeO_4^{2-}$), tellurite ($TeO_3^{2-}$) and elemental tellurium ($Te^0$), which occurs in the form of a blackish or silver solid. As one of the rarest metals on earth, it has an estimated concentration of 0.027 parts per million (ppm) in the planet's crust [20]. In the lithosphere, the metal is found in copper ores, and together with other metals such as gold (in the mineral form of calaverite) and silver (in the mineral form of sylvanite). Tellurium has a low solubility in its +6 oxidation state as tellurate, which is the predominant oxidation state found in the hydrosphere. In the form of the oxyanions of TeIV and TeVI, tellurium is considered a highly toxic element. The antibacterial activity of TeIV has been shown to have inhibitory effects in *Escherichia coli* (*E. coli*) bacteria at concentrations lower than 1 µg/L [21].

Tellurium has been used in solar cell technology [22, 23], photoconductors [24], and thermoelectric devices [25]. New materials based on tellurium have been developed using tellurium, such as fluorescent quantum dots for imaging techniques or photoconductor materials, since tellurium is a p-type semiconductor with a small direct energy bandgap of 0.33 eV at room temperature [26].

Tellurium nanoparticles can be synthesized using different approaches including physical methods, such as laser ablation [27], solvothermal techniques [28], and chemical methods such as acid decomposition, catalytic reduction, and precipitation [29, 30]. However, both chemical and physical approaches have drawbacks, such as use of high temperature and pressure, acidic pH of the medium, harsh and sometimes expensive chemicals, and most importantly, the production of toxic by-products which are a threat to the environment. Nanoparticle aggregation may also occur depending on nanoparticle synthesis rate and the approach followed, which is a serious limitation for biomedical applications. Furthermore, tellurium nanoparticles usually require some form of functionalization using organic groups, polymers, or alternative structures, to avoid aggregation and to reduce the toxicity for human cells.

Novel approaches are needed for the synthesis of tellurium nanomaterials as an answer for the challenges discussed above. Although biogenic or biosynthetic generation of nanomaterials has been used as an alternative to traditional methods involving chemical and physical processes [31], there are a limited number of studies related to the biogenic or "green" synthesis of tellurium nanomaterials. The green synthesis of nanostructures using starch [32] and bacteria [33, 34] have been published, highlighting the potential of tellurium for biomedical and sensing applications.

Compounds employed for the synthesis of metallic nanoparticles can be obtained from plant extracts. Among them, aloe vera extract has been applied for the synthesis of different nanomaterials containing silver [35] or iron [36], due to the ability of the extract to reduce metallic ions in solution. Aloe vera is considered a medicinal plant with anti-inflammatory, UV protection, and antibacterial properties, and it promotes wound and burn healing [37, 38]. The presence of lignin, hemicellulose, and pectins in aloe vera extracts is thought to be responsible for the reduction of metallic ions [39], and it is hypothesized that aloe vera proteins are weakly adsorbed to the metal atoms, functioning as complexing agents.

SUMMARY

Tellurium nanostructures are synthesized through the use of an aloe vera extract to carry out tellurite reduction. The tellurium nanostructures possess antibacterial activity toward both Gram-negative and Gram-positive bacteria but show no significant cytotoxicity toward fibroblasts at antibacterial concentrations. The tellurium nanostructures also possess an anticancer effect, causing a consistent delay in melanoma cell growth over nanoparticle concentrations from 5 µg/mL to 100 µg/mL.

The present technology can be further summarized by the following features.

1. Coated tellurium nanostructures comprising (i) a core comprising amorphous tellurium and (ii) a coating comprising material derived from an aloe vera extract, the coating having an average thickness of at least 1 nm.

2. The nanostructures of feature 1, wherein the nanostructures comprise nanorods and/or spherical nanoparticles.

3. The nanostructures of feature 2, comprising nanorods having an average length of 100±19 nm and an average width of 5±2 nm.

4. The nanostructures of feature 2 or 3, wherein the nanostructures comprise nanoparticles with an average diameter in the range from about 50 to about 250 nm.

5. The nanostructures of any of features 1-4, wherein the coating oxygen at a concentration of about 36 atomic % and carbon at a concentration of about 36 atomic %.

6. The nanostructures of any of features 1-5, which do not comprise tellurium having a hexagonal crystalline structure.

7. The nanostructures of any of features 1-6 that are capable of inhibiting proliferation of cancer cells without significantly inhibiting the proliferation of normal cells of a human subject.

8. The nanostructures of feature 7, wherein the cancer cells are melanoma cells and the normal cells are dermal fibroblasts.

9. The nanostructures of any of features 1-8, that are capable of inhibiting the growth of bacterial cells.

10. The nanostructures of feature 9, that are capable of inhibiting the growth of Gram positive bacterial cells.

11. The nanostructures of feature 9 or 10, that are capable of inhibiting the growth of Gram negative bacterial cells.

12. A method of producing coated tellurium nanostructures, the method comprising:
   (a) mixing an alkali metal tellurite salt with an aqueous extract of aloe vera to obtain a suspension comprising sodium tellurite, aloe vera, and water; and
   (b) heating the mixture in a sealed reaction vessel to about 40° C. to about 80° C. for about 3 hours to about 8 hours;
   whereby coated tellurium nanostructures are produced.

13. The method of feature 12, further comprising:
   (c) centrifuging the product resulting from step (b) to obtain a pellet;
   (d) resuspending the pellet in water; and
   (e) lyophilizing the resuspended pellet.

14. The method of feature 12 or 13, wherein the coated tellurium nanostructures resulting from step (b) comprise nanoparticles, nanorods, or a mixture thereof.

15. The method of any of features 12-14, wherein the temperature in step (b) is from about 50° C. to about 70° C.

16. The method of any of features 12-15, wherein in step (b) heating is performed for about 4 hours to about 7 hours.

17. The method of any of features 12-16, wherein the coated tellurium nanostructures each comprise (i) core comprising or consisting essentially of amorphous tellurium and (ii) a coating derived from material of the aloe vera extract, the coating having an average thickness of at least about 1 nm.

18. The method of any of features 12-17, wherein the alkali metal tellurite salt is selected from the group consisting of sodium tellurite, lithium tellurite, potassium tellurite, rubidium tellurite, cesium tellurite, and francium tellurite.

19. The method of any of features 12-18, wherein the aqueous aloe vera extract is obtained by boiling diced aloe vera leaves in water for about 30 minutes.

20. A method of inhibiting proliferation of bacteria, the method comprising contacting the bacteria with the coated tellurium nanostructures of any of features 1-11, or coated tellurium nanostructures obtained by the method of any of features 12-19.

21. The method of feature 20, wherein the growth of Gram positive bacteria is inhibited.

22. The method of feature 20 or feature 21, wherein the growth of Gram negative bacteria is inhibited.

23. The method of any of features 20-22, wherein contacting is performed by administering the coated tellurium nanostructures to a subject having a bacterial infection, and wherein proliferation of bacteria in the subject is inhibited but proliferation of normal cells of the subject is not significantly inhibited.

24. A method of inhibiting proliferation of a cancer cell, the method comprising contacting the cancer cell with coated tellurium nanostructures of any of features 1-11, or coated tellurium nanostructures obtained by the method of any of features 12-19.

25. The method of feature 24, wherein the contacting is performed by administering the coated tellurium nanostructures to a subject having a cancer, and wherein proliferation of cancer cells in the subject is inhibited but proliferation of normal cells of the subject is not significantly inhibited.

26. The method of feature 24 or feature 25, wherein the cancer cells are melanoma cells and the normal cells are dermal fibroblasts.

27. The method of any of features 23, 25, or 26, wherein the subject is human.

DETAILED DESCRIPTION

Figure 1A:
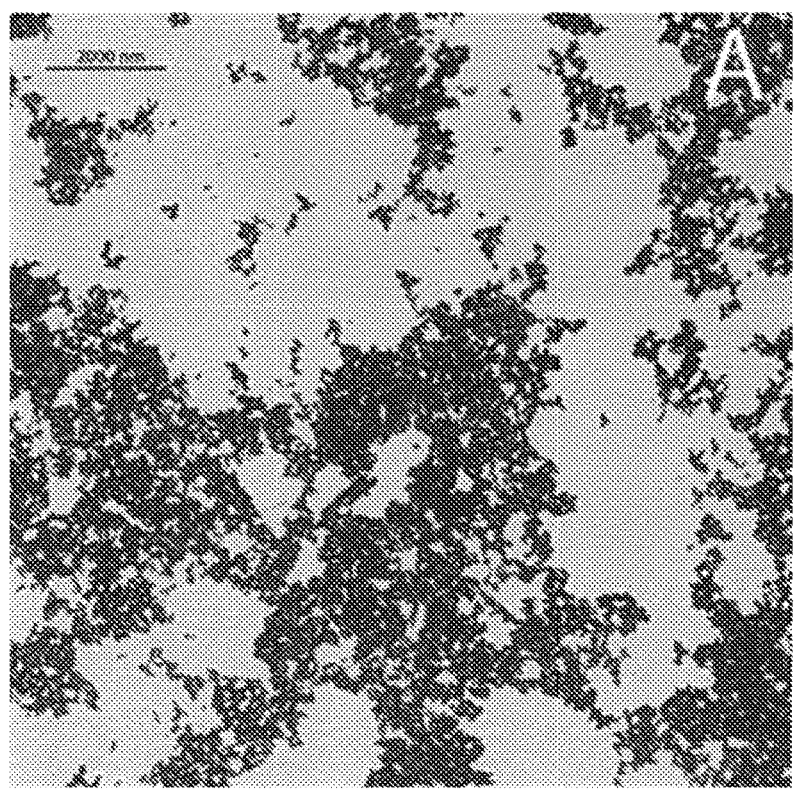
FIG. 1A shows a transmission electron microscopy (TEM) image of green-synthesized AV-TeNP clusters (aloe vera-mediated tellurium nanoparticle clusters).

The present technology provides tellurium nanostructures, including nanorods and nanoparticles, synthesized utilizing aloe vera green chemistry. The tellurium nanostructures have antimicrobial and anticancer properties and can inhibit the growth of microbes and cancer cells while allowing normal cells to propagate. Synthesis methods provided herein can produce tellurium nanostructures without the use of harsh chemicals and without producing toxic byproducts.

Aloe vera gel or mucilage consists of 99.3% water, while the remaining 0.7% is made up of solids with a high content of glucose and mannose. The leaves possess anti-inflammatory activity, UV protection, anti-arthritic properties, promote wound and burn-healing, as well as reported antibacterial properties, due to the presence of a large number of biologically active constituents, such as lignin, hemicellulose or pectins. Furthermore, many other different phytoconstituents such as vitamins, minerals, sugars, anthraquinones, saponins, salicylic acid and amino acids are found in the extracts. Once tellurium ions are reduced by the aloe vera extract and tellurium nanostructures start to nucleate, proteins are weakly bound and act as a complexing agent, stabilizing the nanostructures and avoiding aggregation due to surface charges. Tellurium nanostructures can be prepared with aloe vera extracts through a microwave-assisted method, an oven heating method, or with any suitable heat source. The resulting tellurium nanostructures can be purified, such as by centrifugation and washing, or by other known methods.

To prepare a suitable aloe vera extract, aloe vera leaves were purchased from a local vendor and sterilized to remove potential contaminants. 100 grams of aloe vera leaves were finely cut into small pieces and boiled in a 500 mL beaker together with 100 mL of deionized water for 30 minutes. During that time, the initially clear water turned brownish. After boiling, the solution was cooled and filtered using a 0.2 μm pore size filter coupled with a vacuum. The cooled brownish leaf broth was then stored in the refrigerator at 4° C. prior to use in experiments as the unique liquid medium for the synthesis reaction.

A stock solution of 10 mM sodium tellurite (Na$_2$TeO$_3$) was prepared in deionized water and a final concentration of 2 mM in 20 mL of deionized water was mixed with the same amount of aloe vera extract and stirred at room temperature for 15 min. The mixture was then added to a 100 mL, Teflon-lined autoclave reactor and heated in an oven at 60° C. for 5 hours. The reactor was then removed from the oven and opened, and the reactor contained a black suspension of tellurium nanoparticles. The heating can be for about 1 to about 10 hours, for about 2 to about 9 hours, for about 3 to about 8 hours, for about 4 to about 7 hours, or for about 5 to about 6 hours. The temperature can be from about 40° C. to about 90° C., from about 50° C. to about 80° C., from about 55° C. to about 75° C., from about 60° C. to about 70° C., or about 60° C. Pressure developed within the sealed reaction vessel can change time and temperature needed for the reaction. For example, if the reaction is performed at higher pressure, the time and/or temperature of the reaction can be reduced.

Characterization of the reaction product by transmission electron microscopy (TEM) was performed right after the synthesis (see FIGS. 1A, 1B), with no centrifugation or wash procedure employed. Clusters of Te spheres aggregated together with Te nanorods were observed. The resulting black suspension was poured into a 50 mL Falcon centrifuge tube and centrifuged at 10,000 rpm for 20 min. A black precipitate formed on the bottom of the tube, which was collected and washed twice with deionized water to remove potential additional compounds from the reaction. The black color of the precipitate supported the presence of an amorphous phase of Te. After the washes, the pellet was mixed and homogenized with 5 mL of deionized water and refrigerated for 4 hours at −80° C. The glass vial containing the frozen solution was lyophilized and left to dry overnight. The powder was then collected, weighed, and dissolved in sterile water for further experiments. The clusters shown in FIGS. 1A and 1B were found to be separated by the purification process (centrifugation and washing). The resulting tellurium nanostructures showed a uniform distribution, with two different morphologies present (see FIG. 2D), nanorods and spherical nanopartices.

Without intending to limit the technology to any particular mechanism, the combination of both a reducing agent and stabilizer in the aloe vera extract is believed to have acted as a shape control agent, bonding different facets of the structure with different degrees of strength, and thereby allowing different faces of the nucleation structures to grow faster than others, producing the elongated rods shown in FIGS. 2A-2D. The absence of debris in the TEM images of the purified nanostructures indicates that purification successfully eliminated by-products from the synthesis.

Figure 2A:
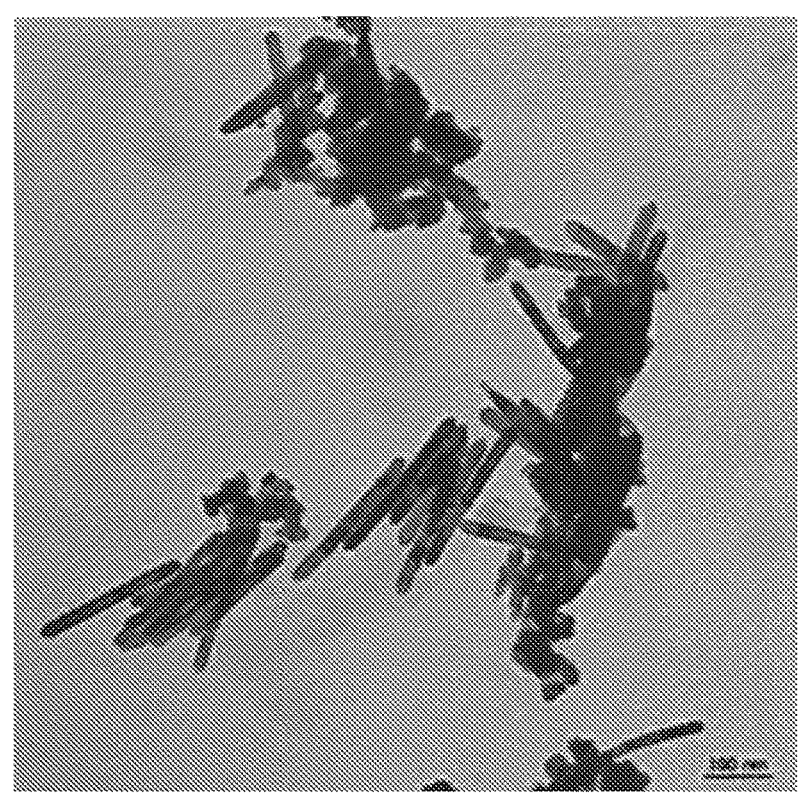
FIGS. 2A-2D show transmission electron microscopy (TEM) images of the aloe vera-mediated tellurium nanostructures. Tellurium nanorods formed aggregates (see FIGS. 2A, 2B, and 2D) with different clusters of amorphous nanostructures including nanoparticles (see FIGS. 2A and 2D).
Figure 2B:
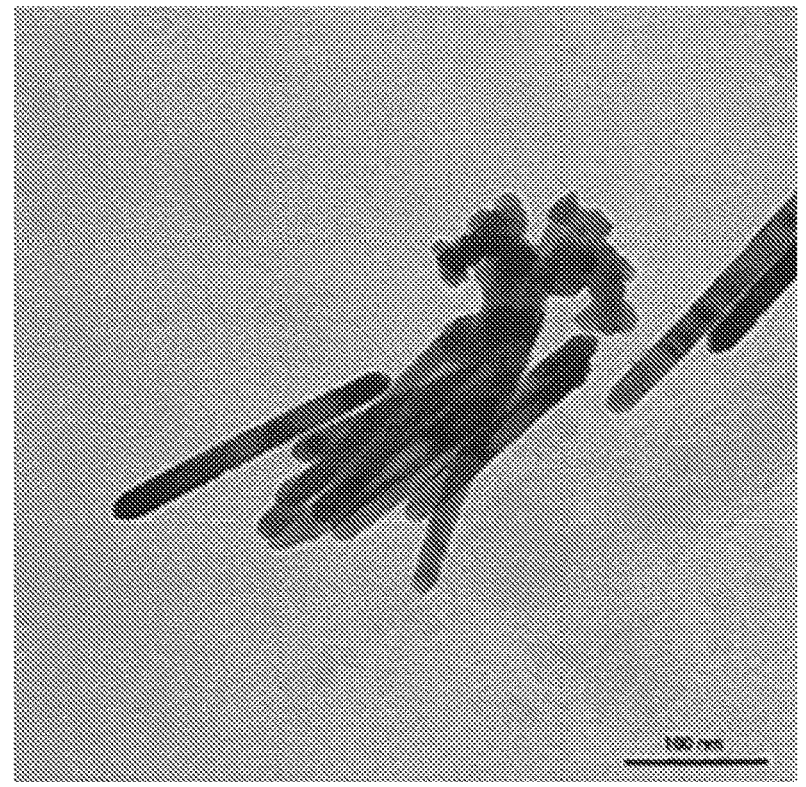
Figure 2C:
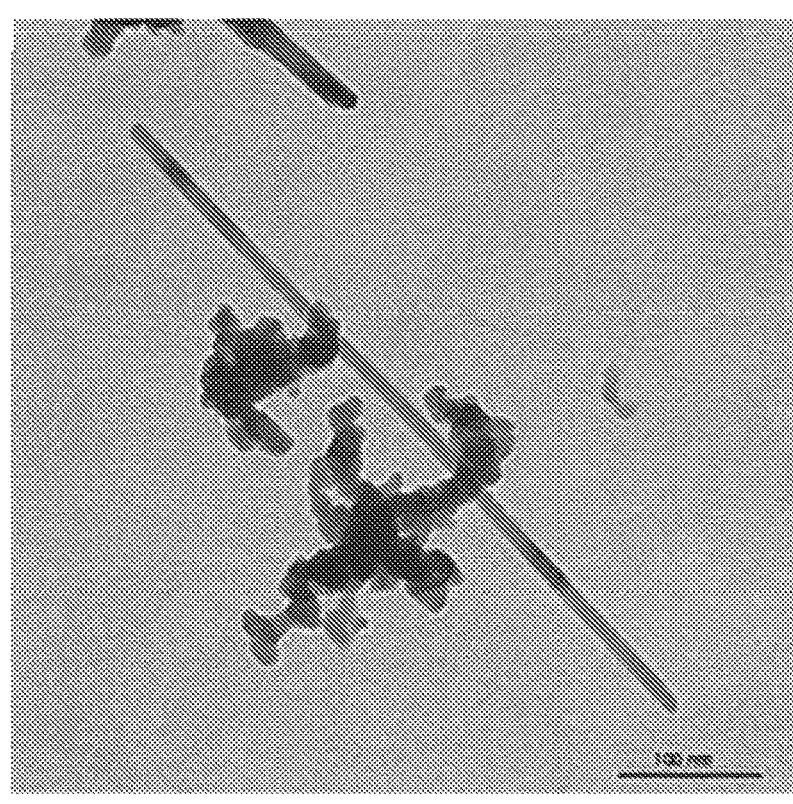
Figure 2D:
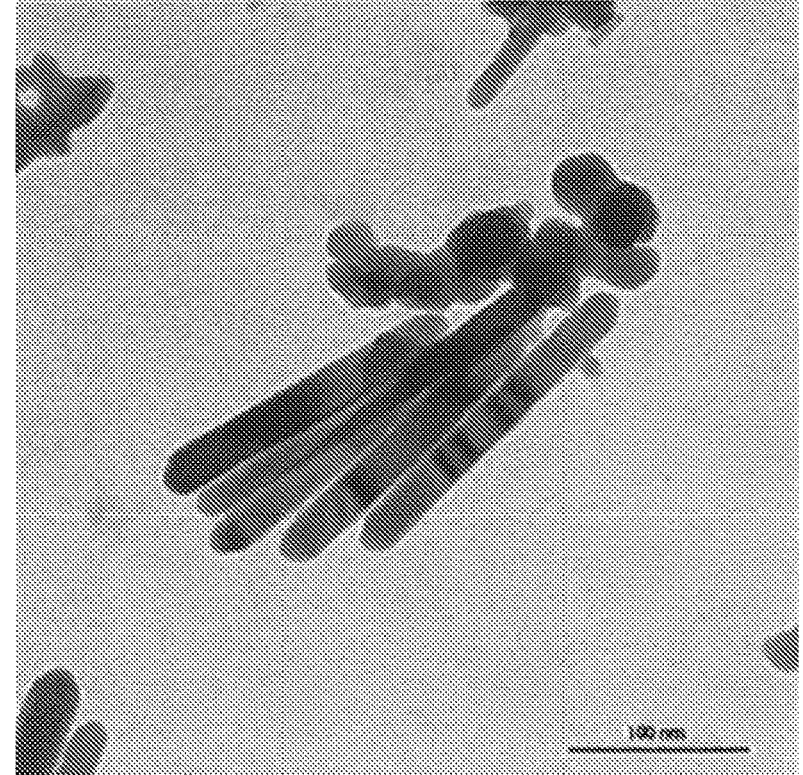

The clusters disassembled and separated after the centrifugation, wash, and lyophilization steps, producing a uniform distribution of nanorods combined with some nanoparticles having an approximately spherical shape (FIGS. 2A-2D). The term "nanoparticles" or "nanospheres" as used herein refers to only the approximately spherical particles and not to the nanorods. "Nanostructures" refers to the combination of nanorods and nanoparticles. Nanorods had a length of 100±19 nm and a width of 5±2 nm and tended to aggregate, forming structures with up to 10 rods together, bound together with some of the nanoparticles. Nanospheres with a size distribution from about 20 to about 60 nm (measured using TEM) aggregated either together (FIG. 4A) or with nanorods (FIGS. 2A-2D). The aloe vera tellurium nanospheres or nanoparticles (AV-TeNPs) seemed to be aggregated to the rods, usually appearing together (FIG. 2A, FIG. 2D). The clusters or aggregates were easily disrupted, and small aggregates were pulled apart after a few minutes of sonication, indicating weak interaction between the nanoparticles. Prominent clustering did not occur over time based on TEM measurements taken directly from the final solution a week after the synthesis. By SEM analysis, a class of AV-TeNPs with larger diameters ranging about 50 nm up to about 250 nm could be seen.

Figure 4A:
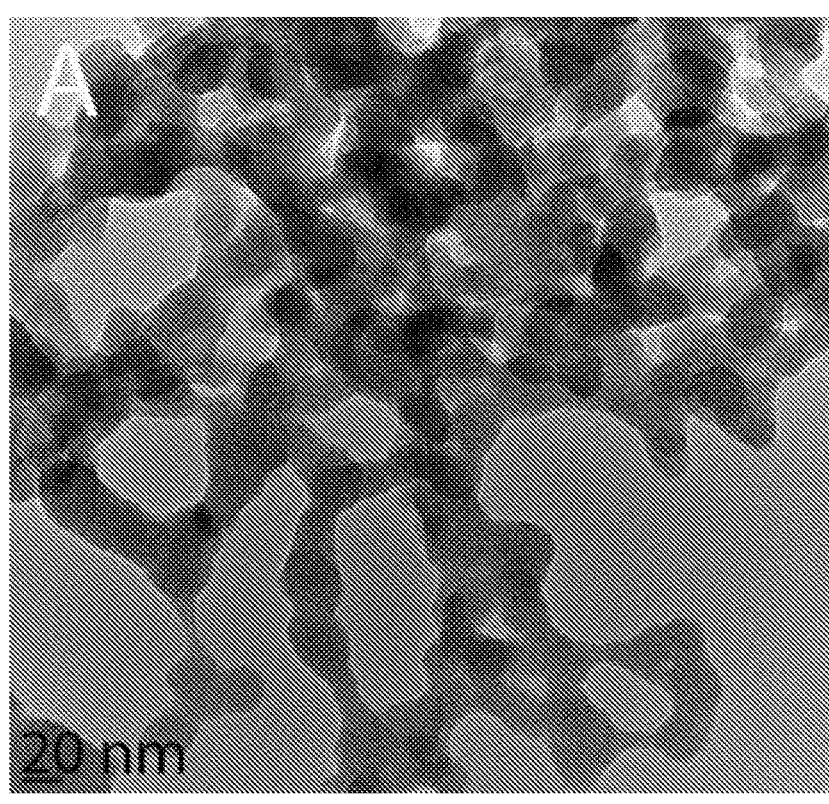
FIG. 4A shows a TEM image of an agglomerate (aggregate) of AV-TeNPs.
Figure 4B:
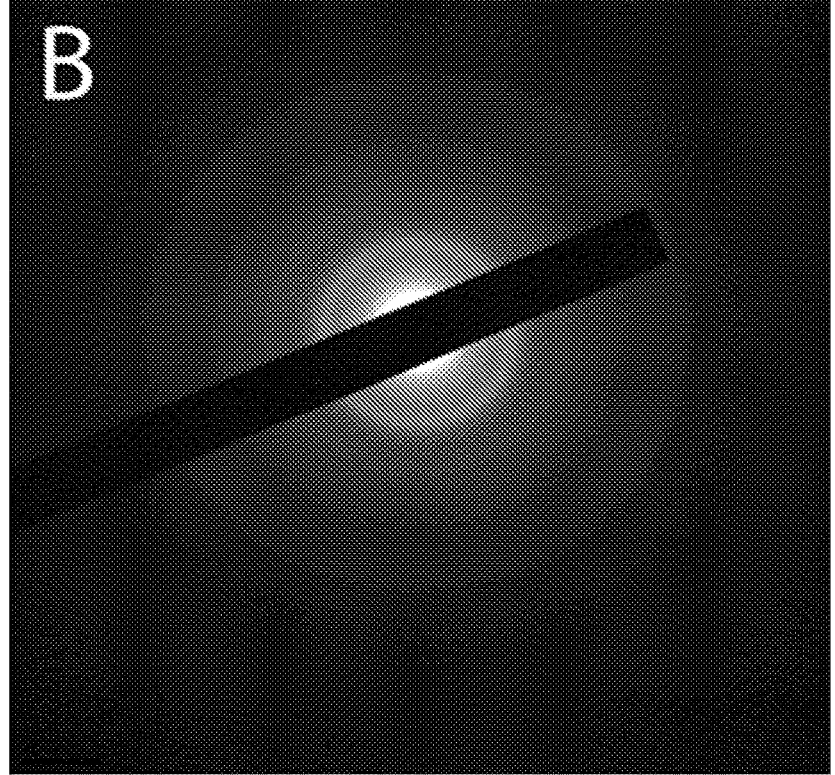
FIG. 4B shows the electron diffraction pattern of the agglomerate of AV-TeNPs shown in FIG. 4A.
Figure 4C:
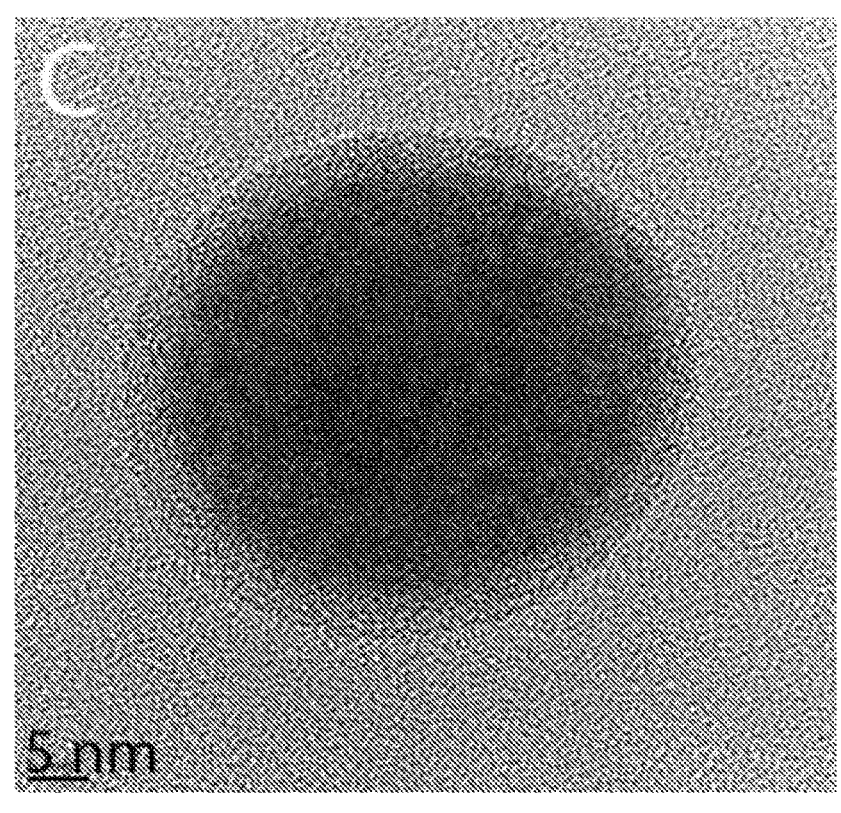
FIG. 4C shows a TEM image of a single spherical nanoparticle of an AV-TeNP.
Figure 4D:
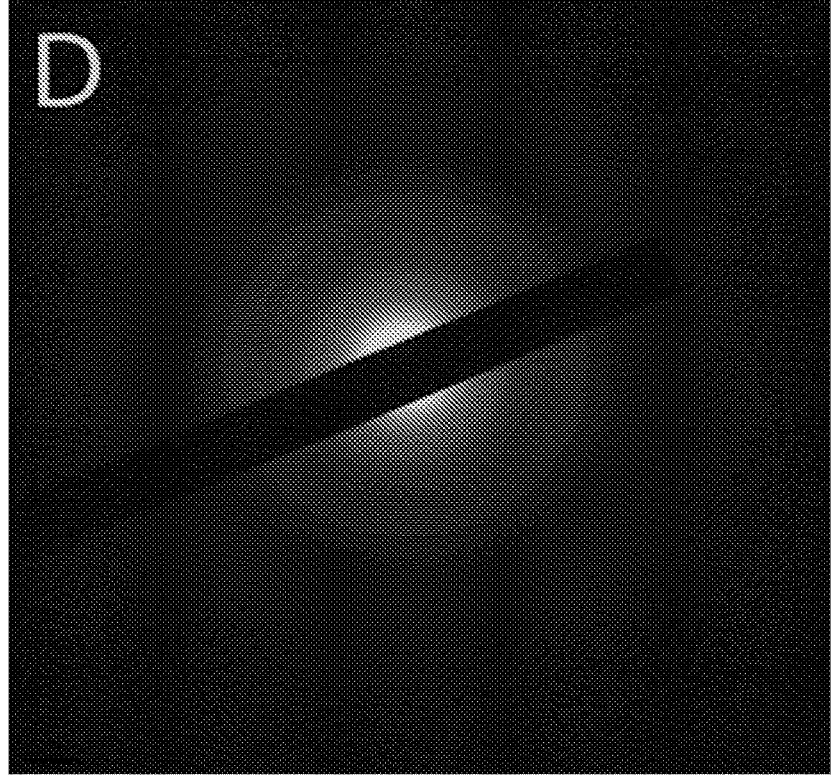
FIG. 4D shows the electron diffraction pattern of the single spherical nanostructure of an AV-TeNP shown in FIG. 4C.
Figure 5:
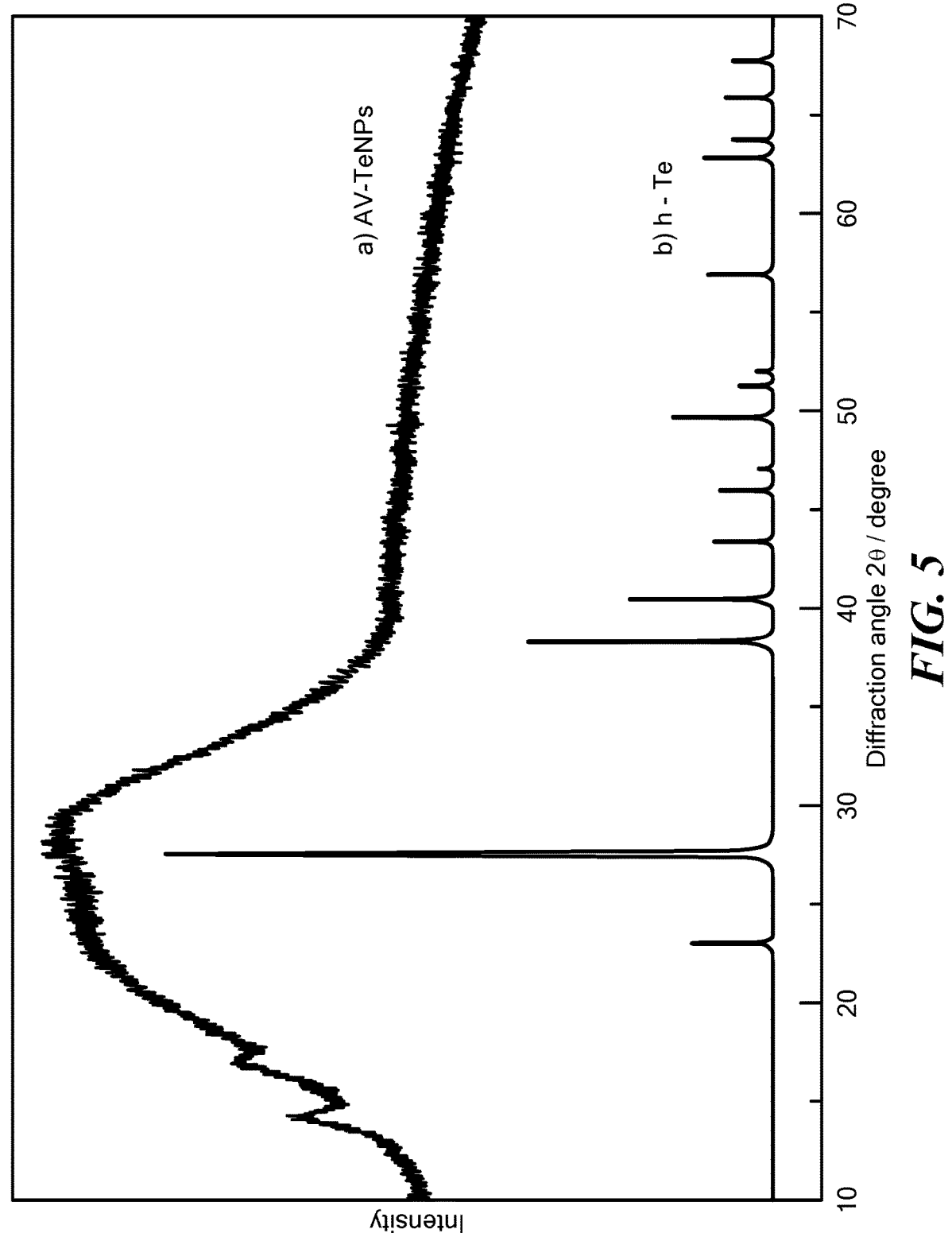
FIG. 5 shows the amorphous XRD spectrum (top spectrum) from an XRD analysis of AV-TeNPs with a calculated XRD pattern of elemental hexagonal tellurium (h-Te) shown in the bottom spectrum.

The nanostructures, including both nanoparticles and nanorods, were shown to contain amorphous (i.e., non-crystalline) tellurium (FIGS. 4B, 4D, 5). In FIG. 5, the calculated XRD spectrum for hexagonal tellurium (h-Te) is shown as the bottom trace, while the actual XRD spectrum of the (amorphous) AV-TeNPs is shown as the top trace. The tellurium in the nanostructures consisted essentially of amorphous tellurium because the XRD spectrum (top trace, FIG. 5) clearly shows a broad peak corresponding to amorphous Te without peaks characteristic of crystalline structure. As it is known that XRD has excellent sensitivity for detecting low levels of crystallinity, the lack of crystalline peaks in the XRD demonstrates a high percentage of amorphous Te structure within the nanostructures. The presence of any significant amount of crystalline Te material would have shown peaks corresponding to crystalline Te in the XRD spectrum. Thus, the Te core of each nanostructure is mostly or entirely amorphous Te.

Figures 8, 9:
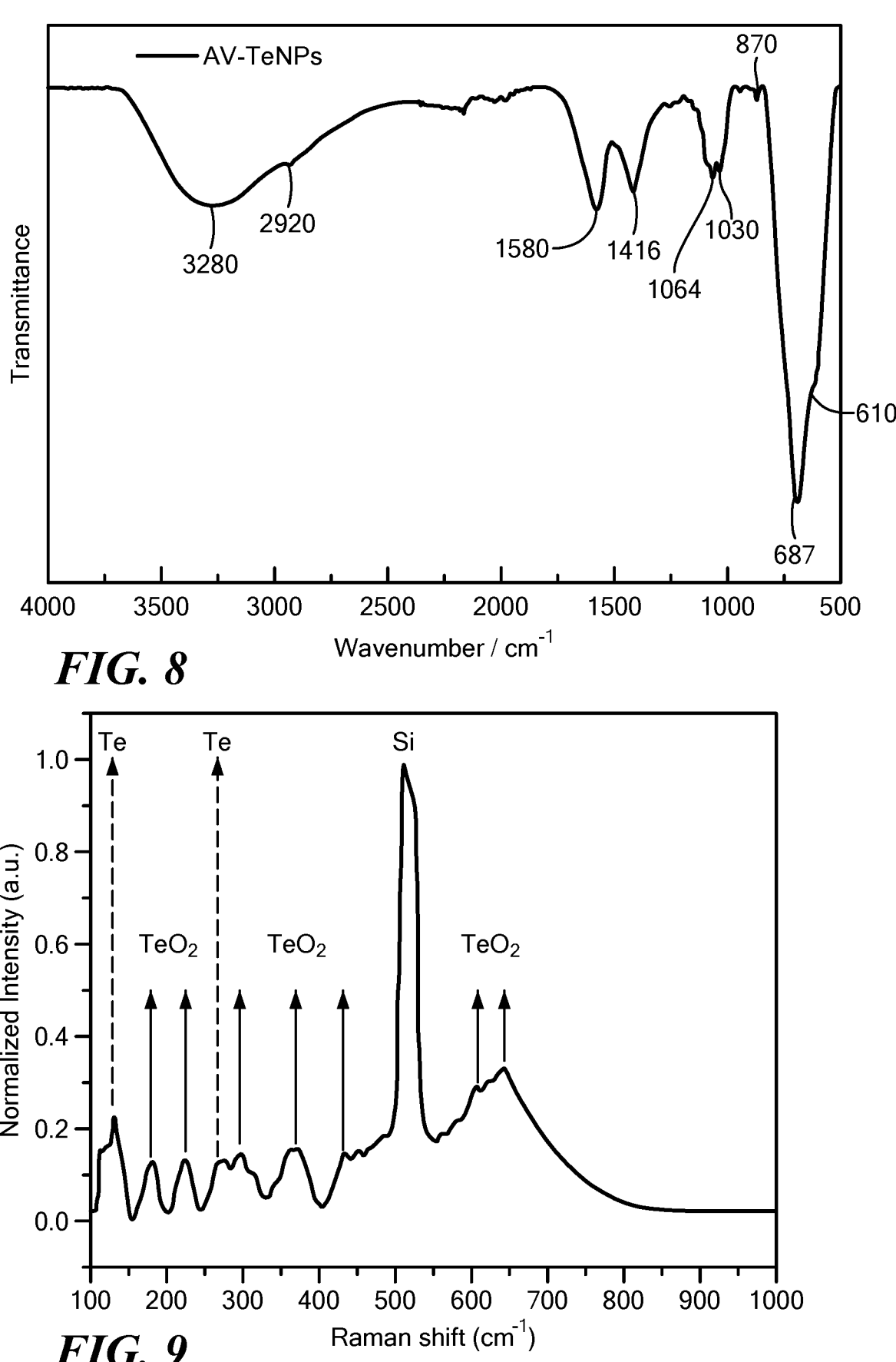
FIG. 8 shows an FT-IR spectrum of the aloe vera-mediated TeNPs (AV-TeNPs). The FT-IR spectrum was acquired in attenuated total reflectance (ATR) mode. The samples for (ATR) FT-IR analysis were prepared by drop casting the Te nanostructure colloids on a sample holder heated at ~50° C. The IR spectra were scanned in the range of 500 to 4000 cm$^{-1}$ with a resolution of 4 cm$^{-1}$.
FIG. 9 shows a Raman spectrum of the AV-TeNPs deposited on top of a silicon wafer. The peaks of Te and TeO$_2$ are clearly identified.

A coating surrounding all of the individual nanostructures was observed (e.g., FIG. 4C). Using FTIR (FIG. 8, ATR mode) and transmission electron microscopy-energy dispersive X-ray (TEM-EDX, FIGS. 6C, 6D), the coating was found to be an organic coating derived from the aloe vera extract.

Figure 3:
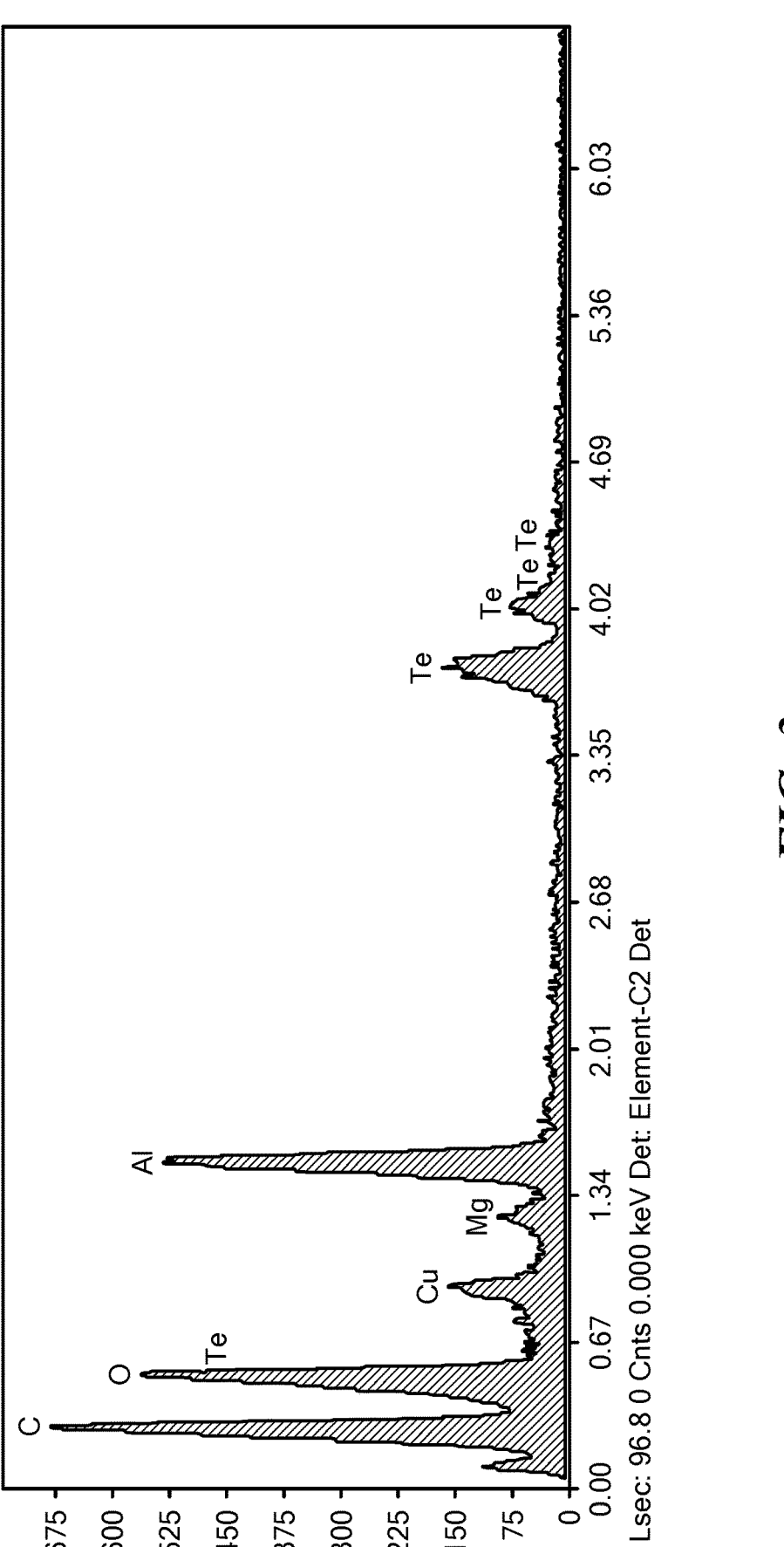
FIG. 3 shows an energy-dispersive X-ray (EDX) spectrum of nanoparticles made by aloe vera extract. Elemental tellurium composition was noticeable, together with the presence of carbon and oxygen.

Energy dispersive X-ray (EDX) of the AV-TeNPs is shown in FIG. 3. In FIG. 3, characteristic peaks for tellurium were found together with carbon and oxygen, confirming the presence of organic material surrounding the nanorods. The presence of aluminum and copper peaks was due to the composition of the sample mount employed for the measurements and the copper grids, respectively.

Figure 6A:
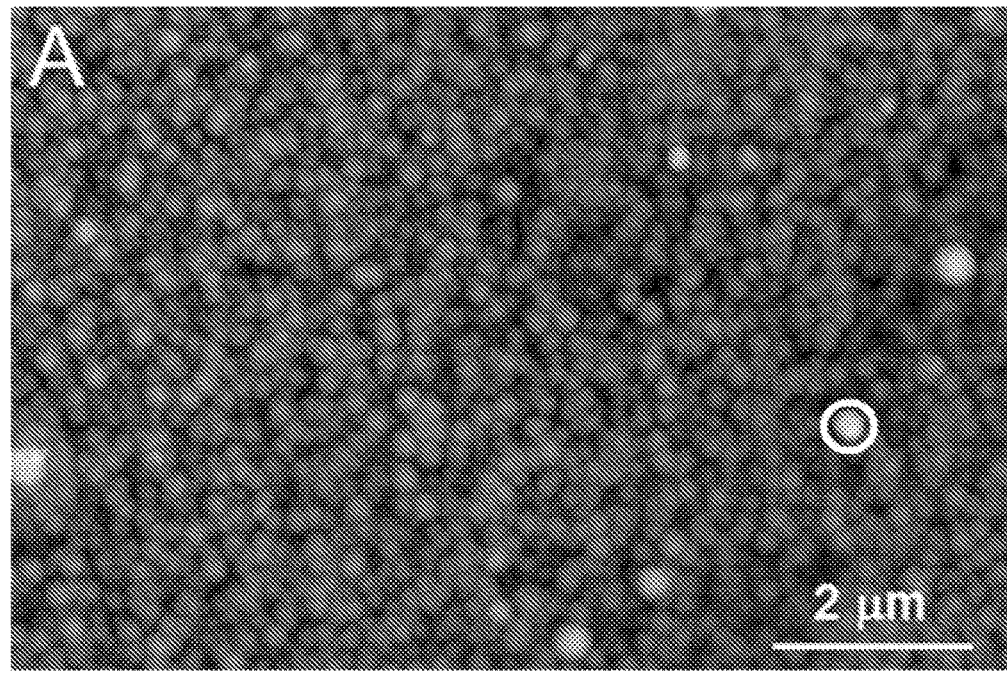
FIG. 6A shows a SEM image of AV-TeNPs; a larger Te nanoparticle is circled.
Figure 6B:
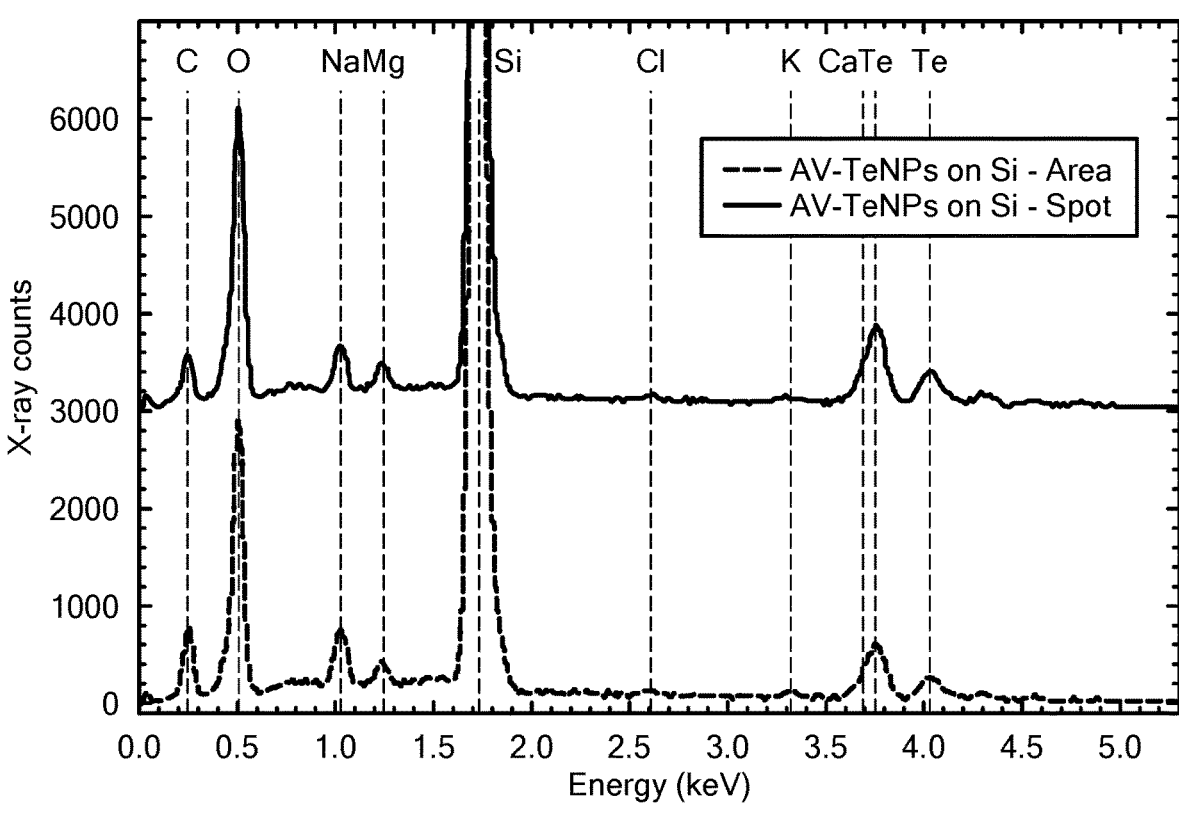
FIG. 6B shows EDX characterization of the AV-TeNPs shown in FIG. 6A; the EDX of the circled nanoparticle (in FIG. 6A) is the top trace in FIG. 6B, and the EDX of the entire image shown in FIG. 6A is the bottom trace in FIG. 6B. The presence of the Si peak is due to the substrate used for sample preparation, but it is not relevant to the analysis of the obtained nanoparticles and surrounding coating composition.
Figure 6C:
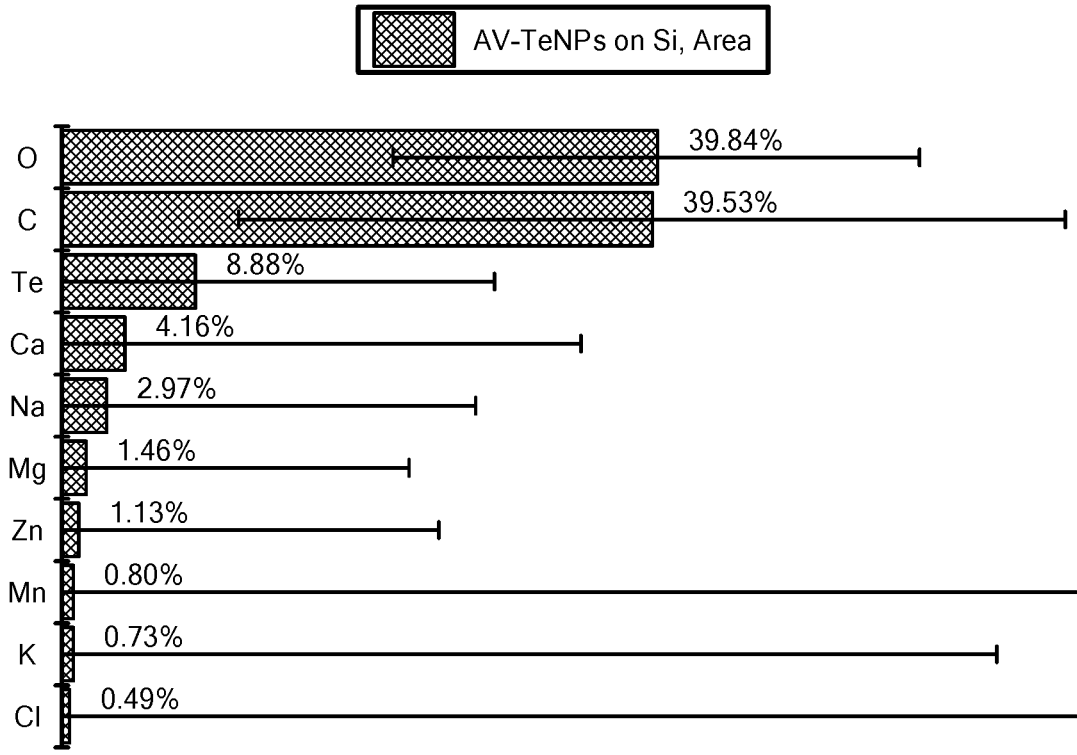
FIG. 6C shows the distribution of the elements from the EDX analysis of the entire area shown in FIG. 6A; the elemental distribution has been renormalized by removing the Si content obtained (see FIG. 6B) and rescaling the rest of elements to add to 100% composition.
Figure 6D:
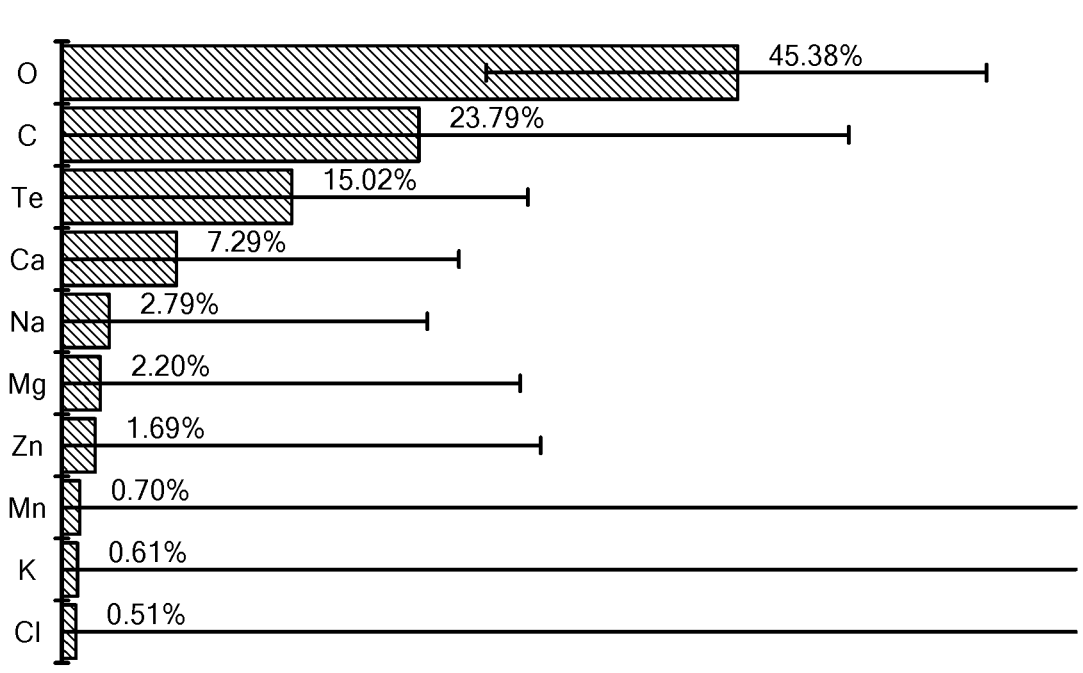
FIG. 6D shows the distribution of the elements from the EDX analysis of the circled larger nanoparticle shown in FIG. 6A; the elemental distribution has been renormalized by removing the Si content obtained and rescaling the rest of elements to add to 100% composition.
Figure 7A:
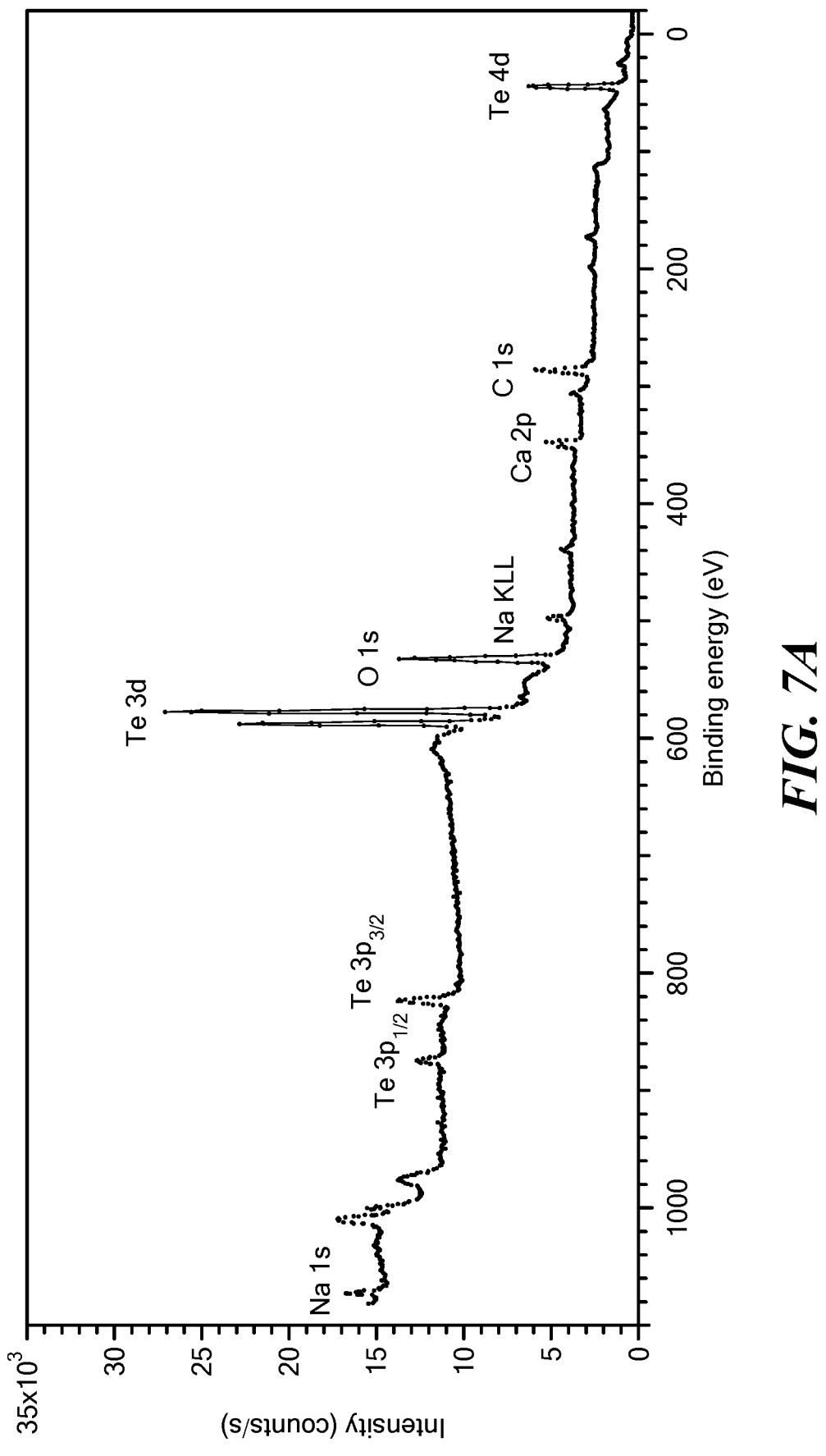
FIG. 7A shows an XPS analysis of AV-TeNPs.

FIG. 6A is a scanning electron microscope (SEM) image of the AV-TeNPs. In FIG. 6A, a larger AV-TeNP is highlighted with a white circle. EDX of the AV-TeNPs shown in FIG. 6A is shown in FIG. 6B. In FIG. 6B, EDX for the entire sample (entire view) shown in FIG. 6A (see bottom trace, FIG. 6B) and for the larger AV-TeNP circled in FIG. 6A (see top trace, FIG. 6B) is compared. The Si peak in FIG. 6B is from the silica substrate and was subtracted out for the elemental analyses shown in FIGS. 6C and 6D. In FIG. 6C, the elemental distribution for the entire image shown in FIG. 6A has been normalized without the Si. In FIG. 6D, the elemental distribution for the circled, larger AV-TeNP in FIG. 6A is shown (normalized without the Si). Broad scan X-ray photoelectron spectroscopy (XPS) of the AV-TeNPs is shown in FIG. 7A. XPS is a much more superficial technique compared to EDX and ATR-IR, therefore the XPS analysis comes mainly from the outer shell of the AV-TeNPs and as a consequence XPS detects mainly the presence of Te oxide. XPS can penetrate about 5-20 Å (0.5-2 nanometers) into a sample, providing insights into the coating on the AV-TeNPs. In Table 1 below, the percent atomic composition from the XPS, the EDX of the whole area (FIG. 6A), and the EDX of the circled particle in FIG. 6A is compared.

TABLE 1

| % Atomic composition of the AV-TeNPs sample extracted from the broad energy range spectrum of the XPS and from EDX analysis. | | | | | |
|---|---|---|---|---|---|
| Technique | C % at | O % at | Te % at | Ca % at | Na % at |
| XPS | 36.4 | 35.8 | 20 | 4.3 | 3.5 |
| EDX, whole area | 39.5 | 39.8 | 8.88 | 4.16 | 2.97 |
| EDX, spot | 23.8 | 45.4 | 15.0 | 7.29 | 2.79 |

The obtained results confirm that the AV-TeNPs contained Te, as well as other elements present in the synthesis precursors; in particular, C and O, Ca, Mg, Zn, Mn, K, and Cl can be found in aloe vera (Hamman 2008). Interestingly, the ratio of Te to O obtained from the full area is lower than that obtained from the circled spot, 0.22 versus 0.33. The spot corresponds to one of the biggest and brightest particles, and therefore this indicates that the Te content is higher in this case, suggesting that the core of the NPs is made of Te. The rest of the elements present in the sample could be either incorporated in the NPs or being part of the organic coating embedding the nanoparticles. In accordance with EDX results (Table 1), principally, O and C were associated with the organic coating coming from the aloe vera extract. Based on further analysis of the organic coating, known compounds in aloe vera (below), and on FIG. 4C, the coating is at least 1 nm thick, or at least 2 nm thick, or at least 3 nm thick, or at least 4 nm thick, or about 5 nm thick. Significant amounts of Ca and Na were detected on the sample. These elements are naturally present in high quantity in aloe vera (Surjushe, Vasani, and Saple 2008). Surprisingly, no relevant presence of nitrogen could be measured at the N 1s core level, which remained within the experimental noise. This is in contrast with other green-synthesized Te nanostructures, in which N was detected (Medina Cruz, González, et al. 2019).

Figure 7B:
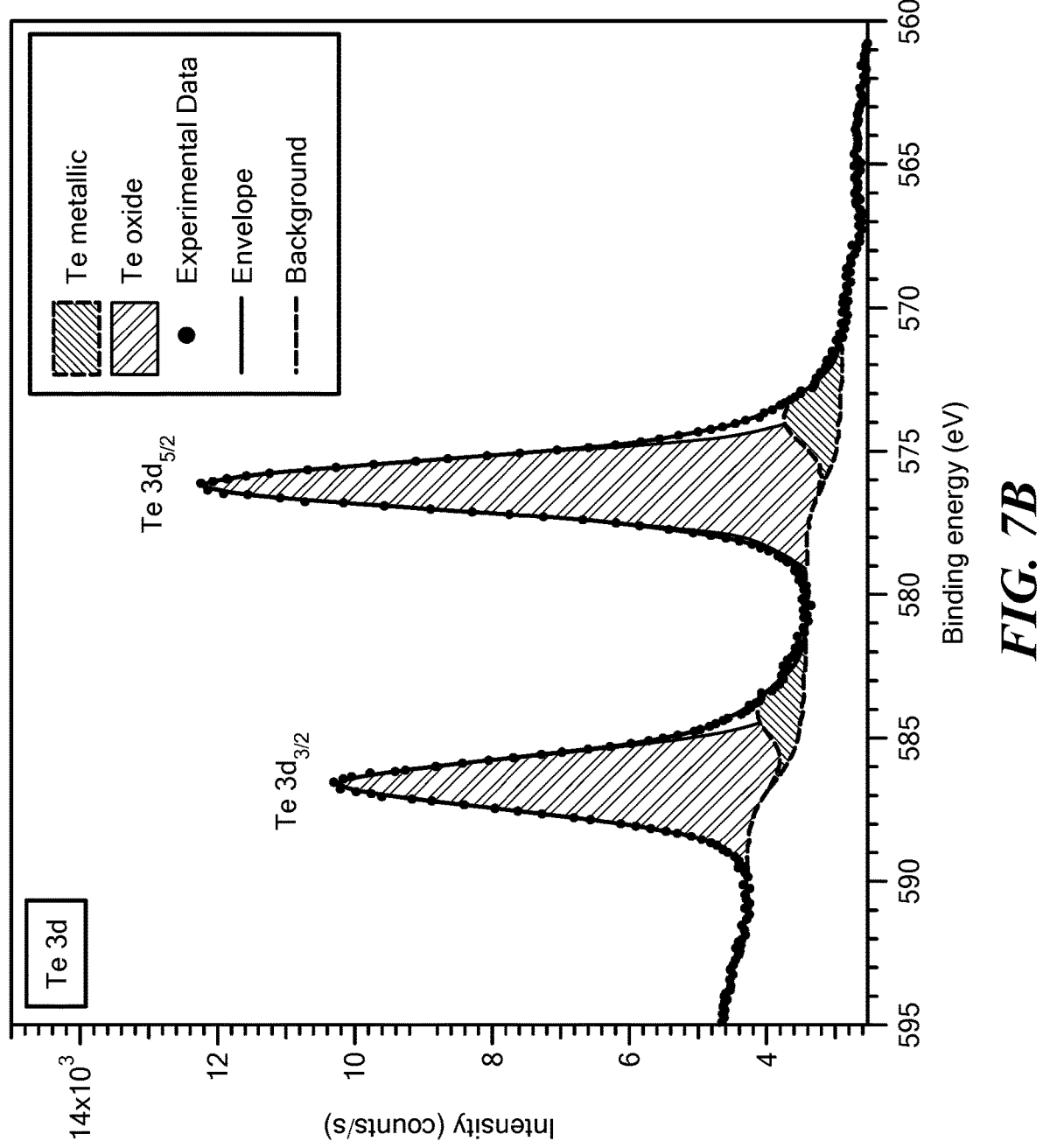
FIG. 7B shown the corresponding metallic and oxide components from the Te 3d XPS shown in FIG. 7A.

The analysis of the Te 3d core level spectrum (FIG. 7B) revealed the presence of a small $Te^0$ component that represented between 4% and 5% of the Te. The metallic and oxide Te 3d 5/2 components were found at 573.8 eV and 576.1 eV. These binding energies are slightly higher than expected (573.0 and 576.0 eV) indicating that charging effects on these Te nanoparticles are stronger than in other compounds.

The majority of the bands observed in the FT-IR spectrum (FIG. 8, ATR) correspond to the functional groups of the most representative phytochemical constituents found in the aloe vera extract, including polysaccharides (e.g. acemannan, galactan and pectin), proteins, vitamins, enzymes, organic acids, phenolic substances, phytosterol, flavones, organic acids and quinones (Lim and Cheong 2015; J P et al. 2016; Medda et al. 2015). In contrast to XPS, the depth of penetration of ATR (FT-IR) can range from about 0.5 microns up to about 5 microns depending upon experimental conditions. The broad band at 3280 cm$^{-1}$ is assigned to the stretching mode of the —OH group from alcohols and phenols. The small vibrational band at 2920 cm$^{-1}$ may be assigned to the symmetrical and asymmetrical C—H stretching of aliphatic —CH and —CH$_2$ groups (Lim and Cheong 2015). The bands at 1580 and 1416 cm$^{-1}$ are characteristic of C═C from aromatic rings and symmetrical —COO stretching vibrations, respectively. The vibrational bands in the region of 1060-1030 cm$^{-1}$ may be responsible for the presence of C—O and C—N stretching vibrations of rhamnogalacturonan, a side-chain constituent of pectins, and aliphatic amines, respectively (Lim and Cheong 2015; J P et al. 2016). The small band at 870 cm$^{-1}$ may be related to the C—H out-of-plane deformation of monosaccharides (J P et al. 2016; Lim and Cheong 2015). Finally, the strong vibrational band at 687 cm$^{-1}$ and the shoulder at 610 cm$^{-1}$ are due to the symmetrical and asymmetrical axial Te—O stretching vibrations (El-Mallawany 1989; Carotenuto et al. 2015). These results demonstrate the presence of organic materials that can be ascribed to the phytochemicals from the aloe vera extract, which act as capping agents of the Te-based NPs. The FT-IR signals of the AV-TeNPs are summarized in Table 2 below.

TABLE 2

FT-IR signals of the AV-TeNPs

| Signal (cm$^{-1}$) | Vibrational modes | References |
|---|---|---|
| 3280 | —OH (phenols and alcohols) | (JP et al. 2016) |
| 2920 | —CH & —CH2 (aliphatic groups) | (Lim and Cheong 2015) |
| 1580 | C═C (aromatic rings) | (JP et al. 2016) |
| 1416 | —COO— (carboxylate groups) | (Lim and Cheong 2015) |
| 1060 | C—O (rhamnogalacturonan) | (Lim and Cheong 2015) |
| 1030 | C—N (aliphatic amines) | (JP et al. 2016) |
| 870 | C—H (monosaccharides) | (Lim and Cheong 2015) |
| 687-610 | Te—O | (El-Mallawany 1989; Carotenuto et al. 2015) |

The Raman analysis (FIG. 9) showed a characteristic peak at 520 cm$^{-1}$, which corresponds to the Si substrate on which the sample (AV-TeNPs) was deposited. The peaks at 132 cm$^{-1}$ (E-bond stretching mode of Te) and 266 cm$^{-1}$ (related to the second order harmonic of the E vibrational mode of Te) correspond to pure Te, hence demonstrating the presence of nanoparticles. On the other hand, the peaks at 180, 224, 296, 368, 434, 606, 642 cm$^{-1}$ correspond to γ-TeO$_2$.

Figure 10A:
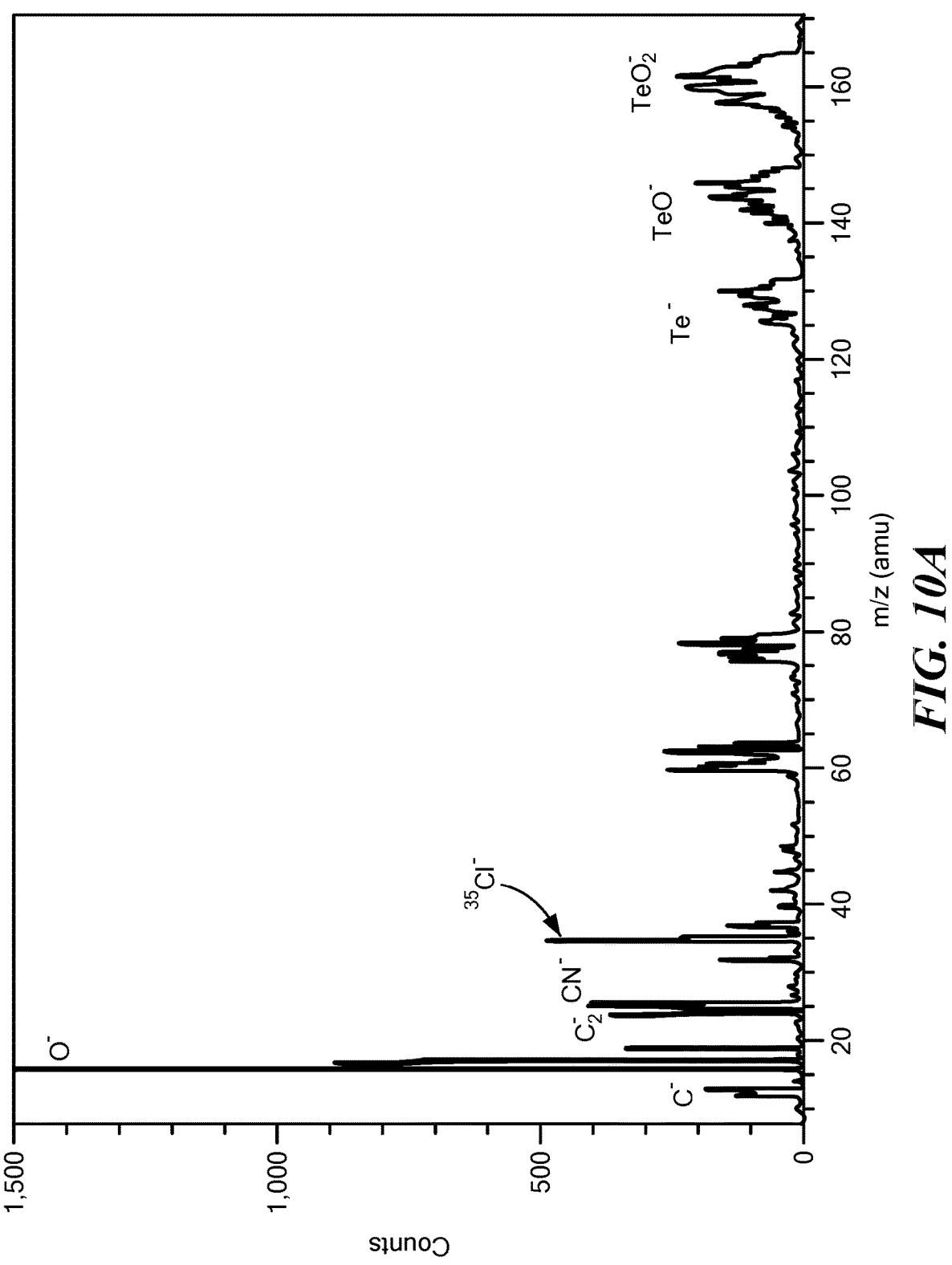
FIG. 10A shows a secondary ion mass spectrum acquired from a 50 μm×50 μm field of view with a 20 keV energy neon ion beam in positive mode.
Figure 10B:
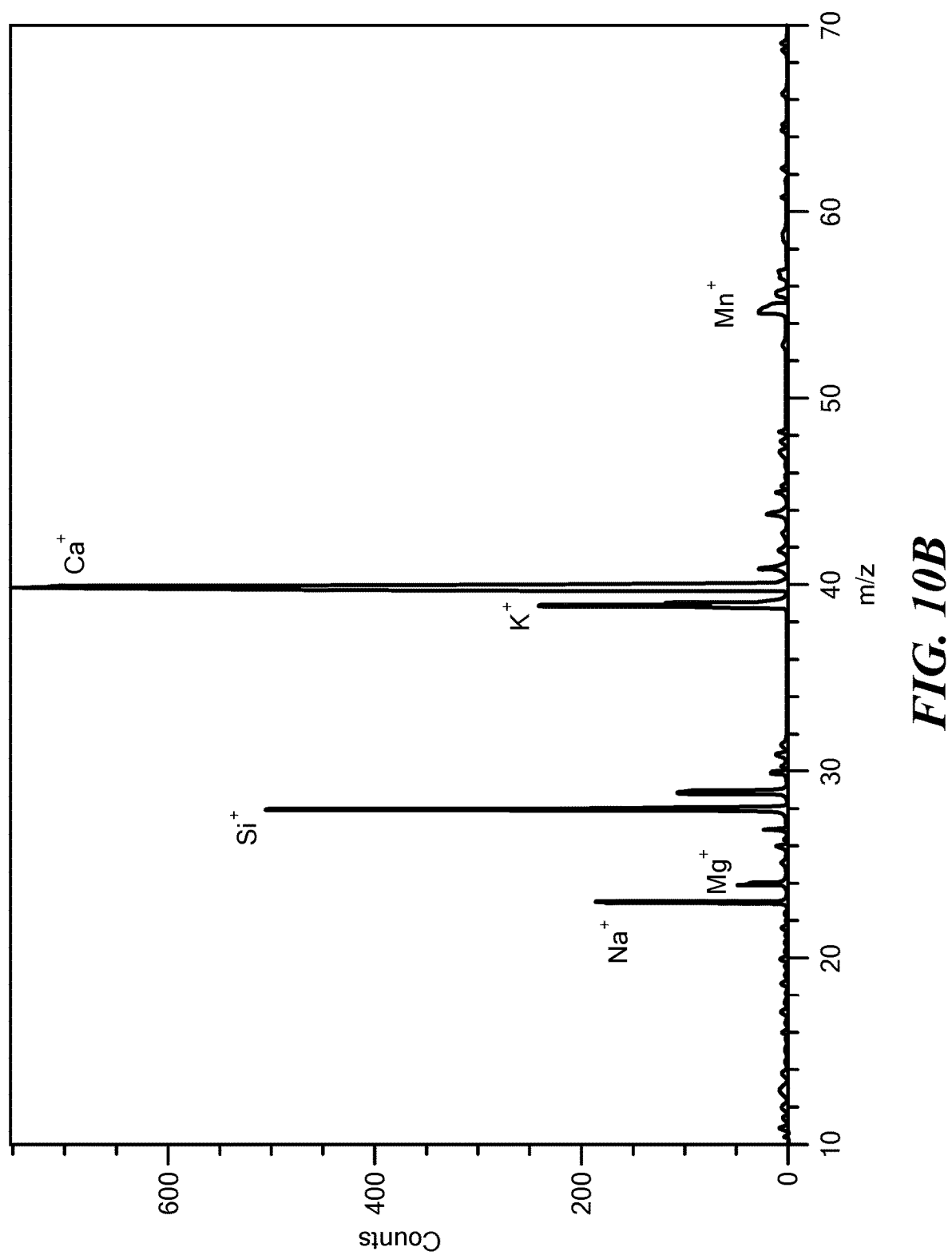
FIG. 10B shows a secondary ion mass spectrum acquired from a 50 μm×50 μm field of view with a 20 keV energy neon ion beam in negative mode.

Secondary ion mass spectrometry (SIMS) imaging was performed on the AV-TeNPs. FIG. 10A shows the mass spectra of positive secondary ions obtained from an AV-TeNPs suspension prepared as a drop on a silicon chip and left to air dry. FIG. 10B shows the mass spectra of negative secondary ions obtained from an AV-TeNPs suspension prepared as a drop on a silicon chip and left to air dry. The elements detected via SIMS are in good agreement with the SEM-EDX analysis except for zinc. The negative mode mass spectrum additionally reveals the presence of CN$^-$, characteristic fragments of organic material in SIMS, as well as TeO$^-$ and TeO$_2{}^-$ clusters ions. The latter could be an indicator of the AV-TeNPs' chemical composition, but the presence of residual Na$_2$TeO$_3$ salts in the solution cannot be excluded.

Proliferation of gram-negative and gram-positive drug resistant bacteria was studied in the presence of AV-TeNPs. Antimicrobial activity of the AV-TeNPs was tested against E.

Figure 11A:
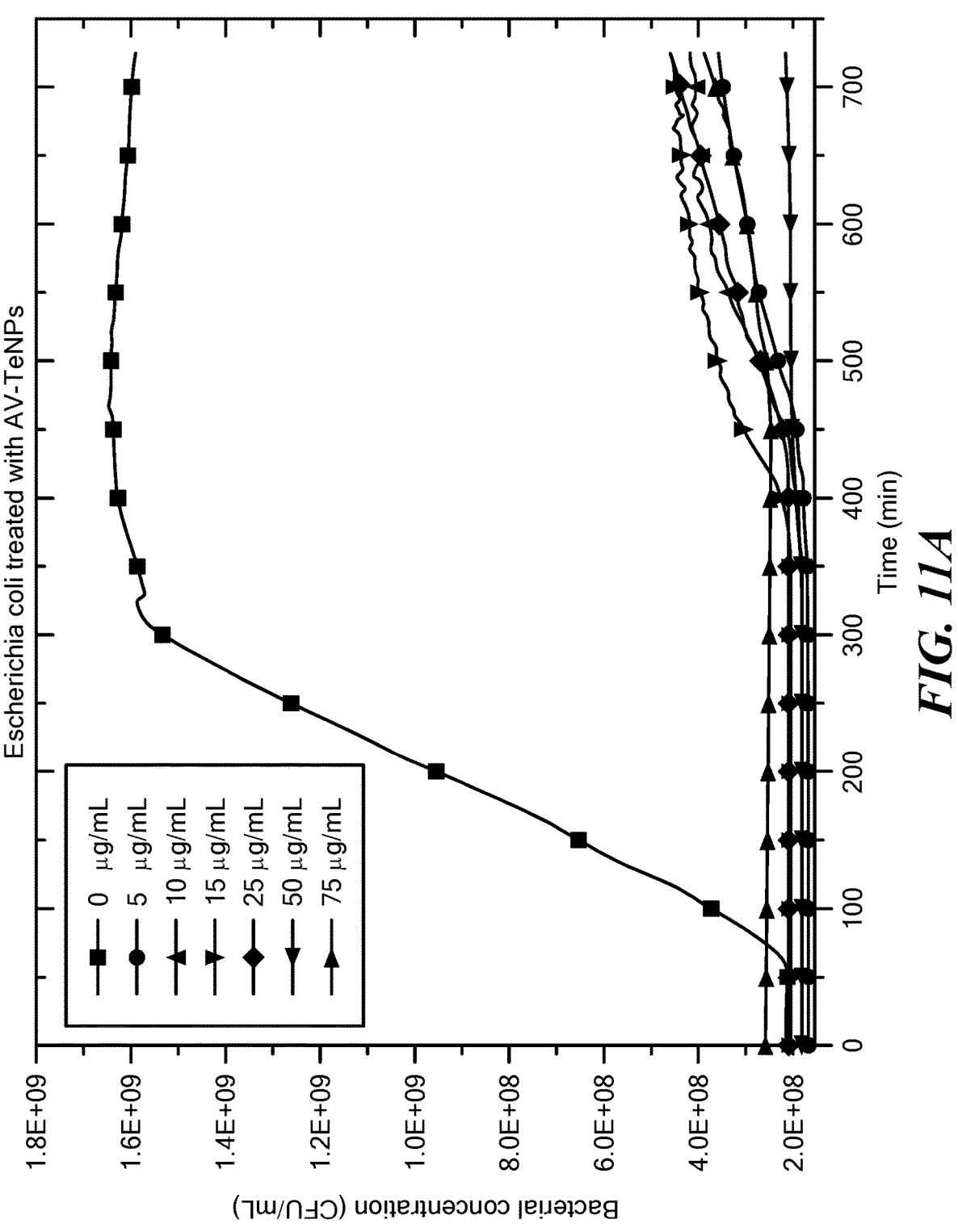
FIG. 11A shows growth of a 10$^6$ CFU mL suspension of E. coli over 24 h in the presence of different concentrations of biogenic AV-TeNPs made by the different bacteria. The values represent the mean±standard deviation, N=3.
Figure 11B:
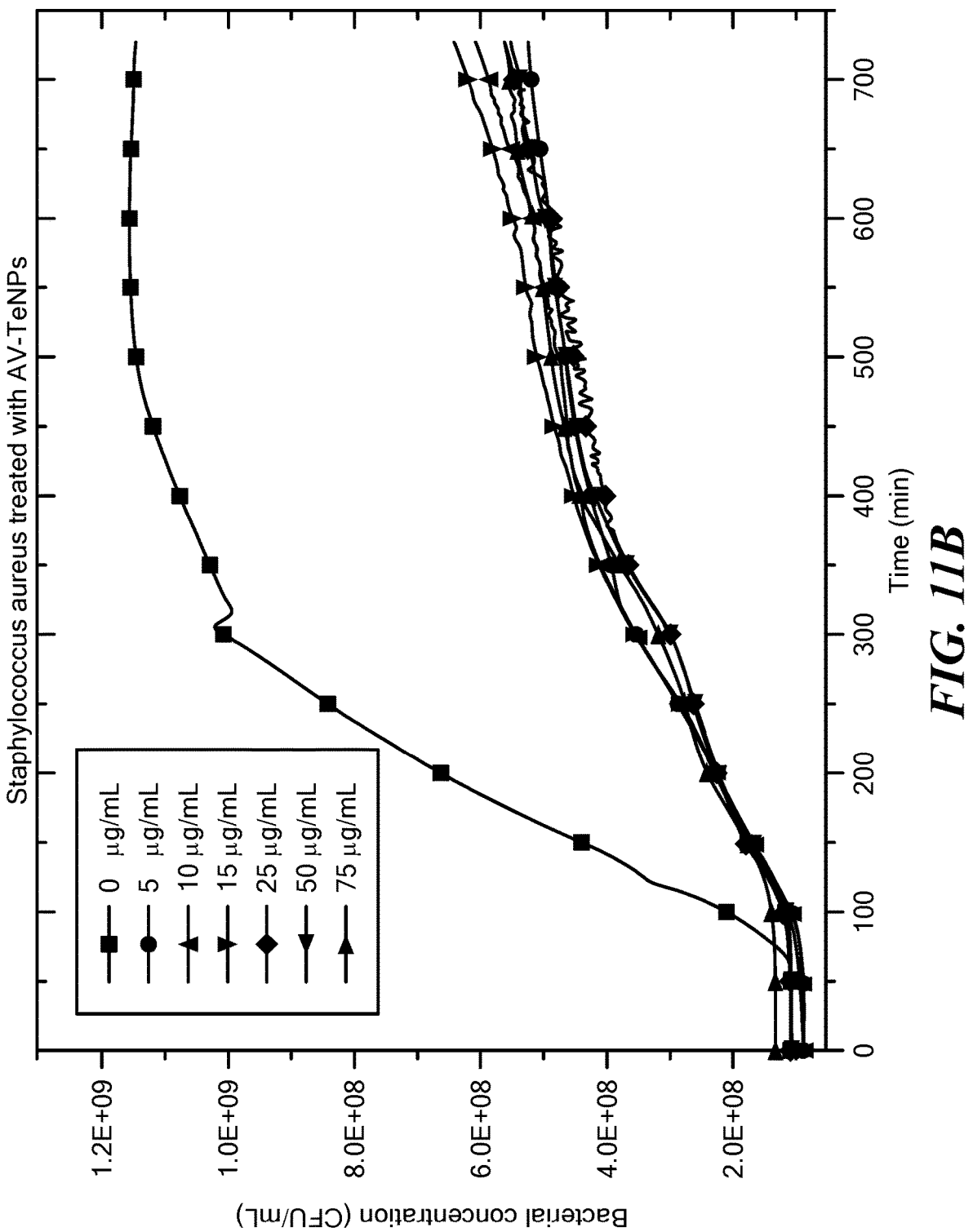
FIG. 11B shows growth of a 106 CFU mL suspension of S. aureus over 24 h in the presence of different concentrations of biogenic AV-TeNPs made by the different bacteria. The values represent the mean±standard deviation, N=3.

10 coli and S. aureus in a range of concentrations between 5 and 75 μg/mL. As seen in FIGS. 11A and 11B, AV-TeNPs caused a large delay and inhibition in the growth of both bacteria. The inhibition is especially noticeable in the case of E. coli. In both bacteria, the concentration of nanoparticles does not seem to show significant differences in the pattern of inhibition. Specifically, FIGS. 11A and 11B show growth of a 10$^6$ CFU mL suspension of E. coli (FIG. 11A) and S. aureus (FIG. 11B) over 24 hours in the presence of different concentrations of biogenic AV-TeNPs made by the different bacteria. The values represent the mean±standard deviation, N=3.

Figure 12A:
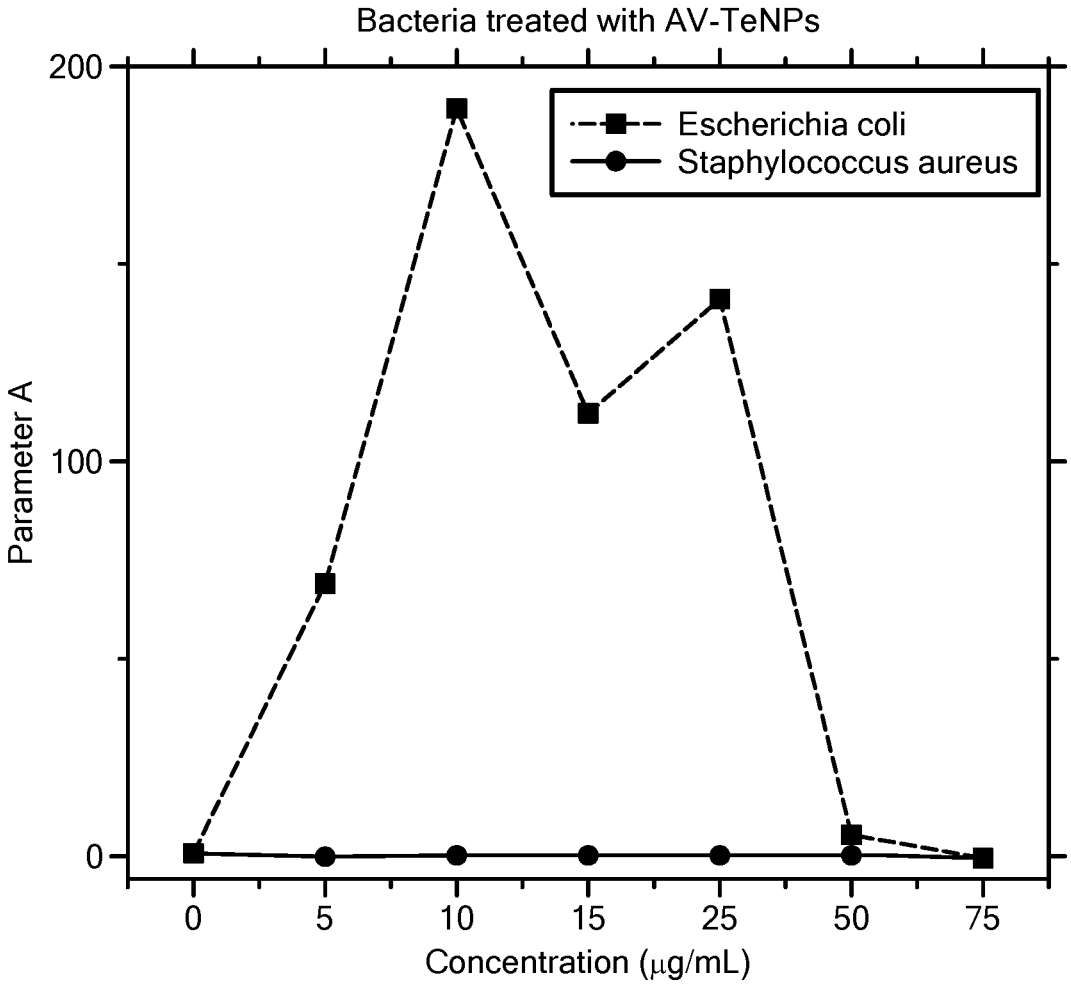
FIG. 12A shows the Gompertz parameters analysis, parameter A, for the treatment of E. coli and S. aureus with AV-TeNPs. The parameter A was analyzed using software.
Figure 12B:
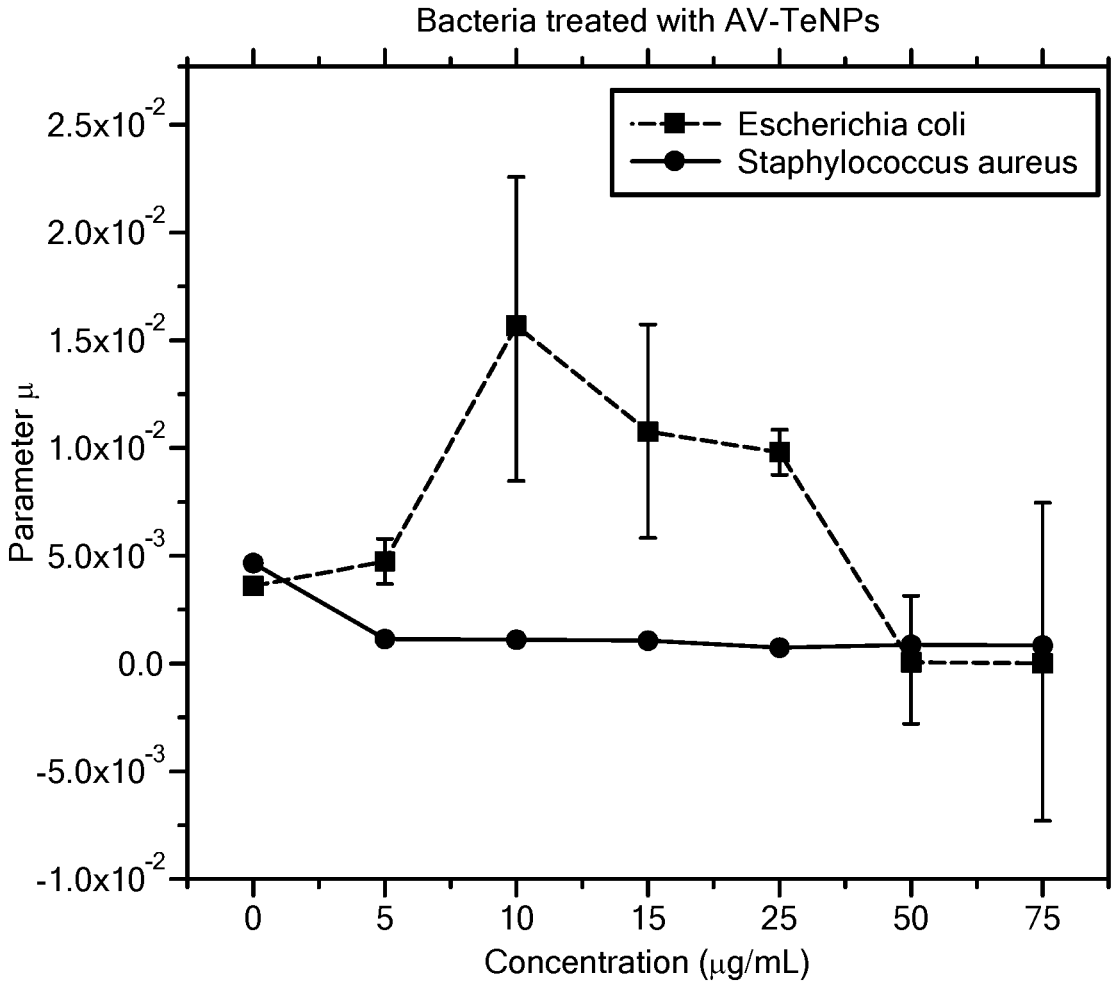
FIG. 12B shows the Gompertz parameters analysis, parameter μ, for the treatment of E. coli and S. aureus with AV-TeNPs. The parameter μ was analyzed using software.

Based on the data in FIGS. 11A and 11B, all the parameters in the Gompertz equation were calculated and plotted for analysis. Parameter A represents the maximum specific growth of the bacteria under experimental conditions. Upon analysis, it was found that a more significant nanoparticle concentration led to a lower asymptotic absorbance value (FIG. 12A). The maximum bacterial growth rate parameter, was also analyzed (FIG. 12B). The plots revealed that a higher AV-TeNP concentration resulted in lower maximum bacterial growth rate.

Figure 12C:
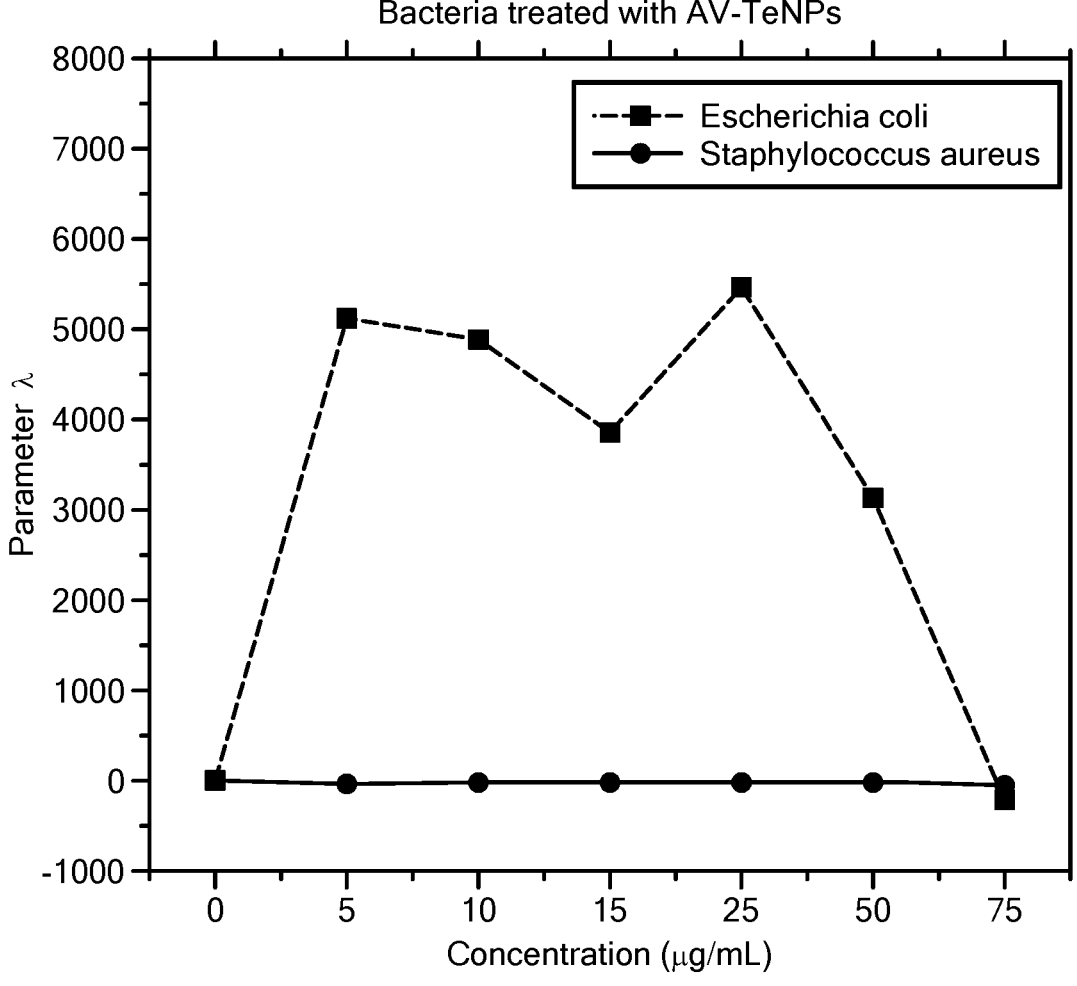
FIG. 12C shows the Gompertz parameters analysis, parameter λ, for the treatment of E. coli and S. aureus with AV-TeNPs. The parameter A was analyzed using software.

Finally, the bacterial lag-time parameter A was analyzed, and results are shown in FIG. 12C. The analysis showed that a higher AV-TeNP concentration led to a shorter lag phase for bacterial growth. Since the lag phase refers to the point where bacteria are adapting to the growth conditions offered by the media, the longer lag phase seen for media with nanoparticles (compared to the control) suggests that the nanoparticle presence delays the maturing of bacteria, slowing their cell division and proliferation. The presence of nanoparticles may affect the bacterial growth cycle through the synthesis of RNA, enzymes, or other molecules involved in this phase [48].

Figure 13A:
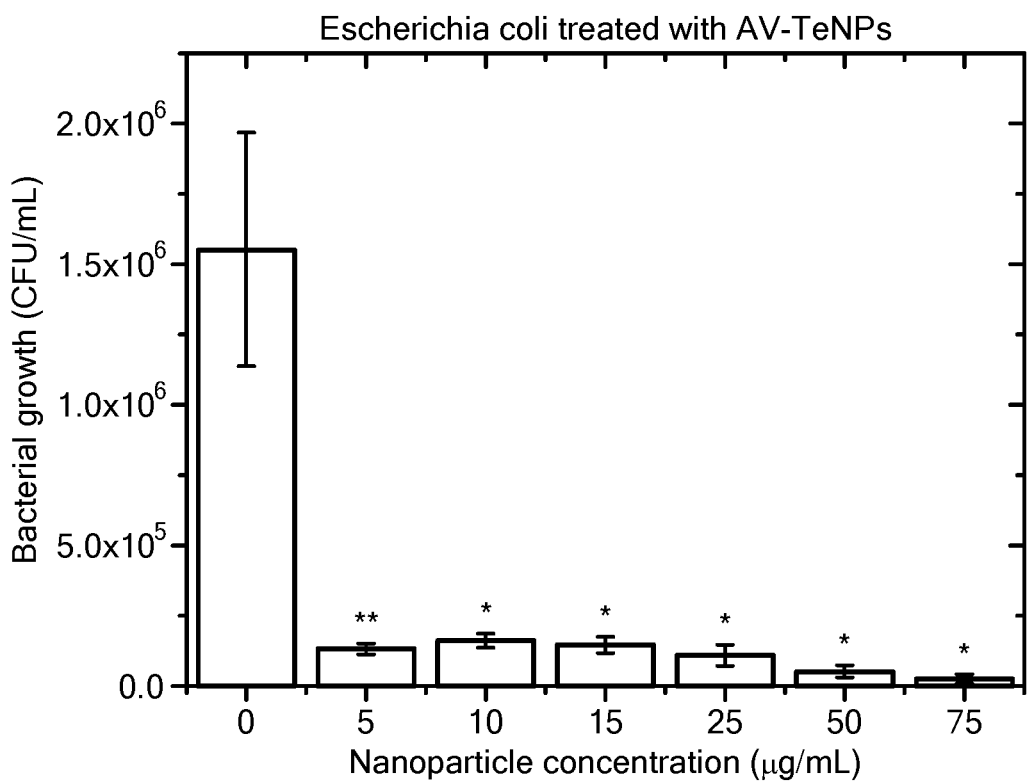
FIG. 13A shows a colony counting assay of E. coli after being treated for 8 hours with AV-TeNPs; N=3; *p<0.01 versus control, **p<0.005 versus control.
Figure 13B:
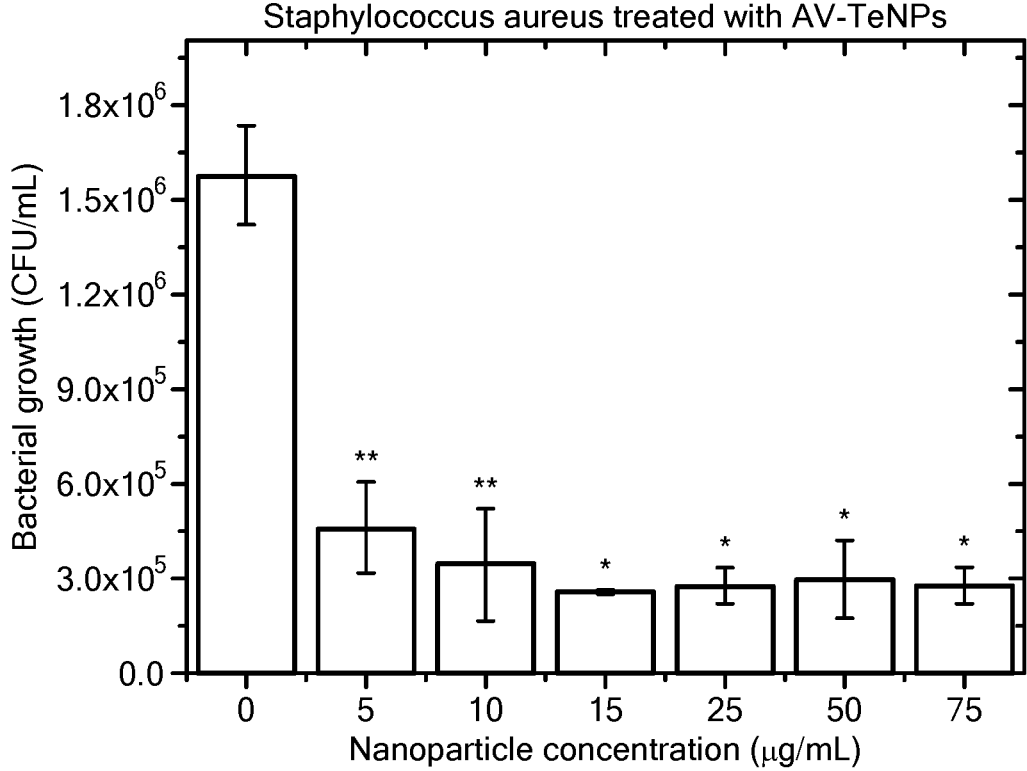
FIG. 13B shows a colony counting assay of S. aureus after being treated for 8 hours with AV TeNPs; N=3; *p<0.01 versus control, **p<0.005 versus control.

Colony counting assays were performed by seeding E. coli and S. aureus bacteria in a 96-well plate and treating with different concentrations of nanoparticles for 8 hours inside an incubator at 37° C. Then, the 96-well plate was removed from the incubator and all the samples were diluted with PBS in a series of vials to either ×100, ×1000 or ×10000. Three drops of a 10 microliter aliquot of each dilution were then placed in a LB-Agar plate and incubated for 8 hours inside the incubator at 37° C. The resulting number of colonies formed in each plate was counted at the end of the incubation. From the colony forming unit assays shown in FIGS. 13A and 13B, it is possible to see that all the nanoparticle concentrations were able to cause a significant delay or inhibition in the bacterial growth. This effect was especially noticeable in the experiments with E. coli. In FIGS. 13A-13B, N=3, *p<0.01 versus control, **p<0.005 versus control.

IC$_{50}$ values were obtained with the aim to show the minimum inhibitory concentration for each one of the bacterial tests. For Escherichia coli experiments, the IC$_{50}$ value was 9.15±2.76 μg/mL, while for Staphylococcus aureus the IC$_{50}$ value was 13.55±4.98 μg/mL. Tellurium nanostructures have been tested against different bacterial strains in the past showing higher MIC values—against Staphylococcus aureus (MIC 250 μg/mL), P. aeruginosa (MIC 125 μg/mL), S. typhi (MIC 125 μg/mL), and K. pneumonia (μg/mL) [49, 50]. Therefore, the aloe, AV-TeNPs have an enhanced antibacterial activity compared to other tellurium nanostructures reported in literature. Based on the IC$_{50}$ values, bacterial growth can be inhibited with as little as about 5 to 20 μg/mL.

Antimicrobial activity of nanoparticles could be due to the production of reactive oxygen species (ROS) within the bacteria upon contact with the AV-TeNPs. ROS are chemically reactive agents containing oxygen within the molecules, such as hydroxyl ($OH^-$) or superoxide ($O^{2-}$) groups. A SEM study of the interaction between bacteria and AV-TeNPs showed that the treatment with the AV-TeNPs induced disruption of the outer cell membrane and cell lysis. This cell membrane damage can be attributed to reactive oxygen species (ROS), although the direct damage of the cells due to the morphology of the nanostructures cannot be discarded.

Toxicity mechanisms towards human cells were evaluated by the analysis of reactive oxygen species (ROS) by exposing melanoma cells to different concentrations of AV-TeNPs at 25 and 100 μg/mL. The cells were in contact with the Te nanoparticles for a period of 24 hours. Therefore, the ROS could be quantified in the cell media. The results (FIG. 14) showed an increase in ROS production when AV-TeNPs were present in the media, with a dose-dependent effect. An excess of levels of ROS in the cell surroundings might lead to substantial damage to proteins, nucleic acids, lipids, membranes and organelles within the cell. Besides, at sufficient doses, powerful oxidants cause severe damage to macromolecules all over the membranes and cytoplasms (Valencia and Moran 2004). This can lead to cell death by apoptosis, and this was observed after an SEM analysis of melanoma cells in presence of AV-TeNPs. It is distinguished by cell shrinking, membrane blebbing, chromatin condensation and nuclear fragmentation, followed by the formation of apoptotic bodies (Manke, Wang, and Rojanasakul 2013).

Furthermore, the presence of phenols and sulfur within the composition of aloe vera extract, which are highly likely to have remained within the structure of the AV-TeNPs, may explain this antiseptic effect [54].

Figure 15A:
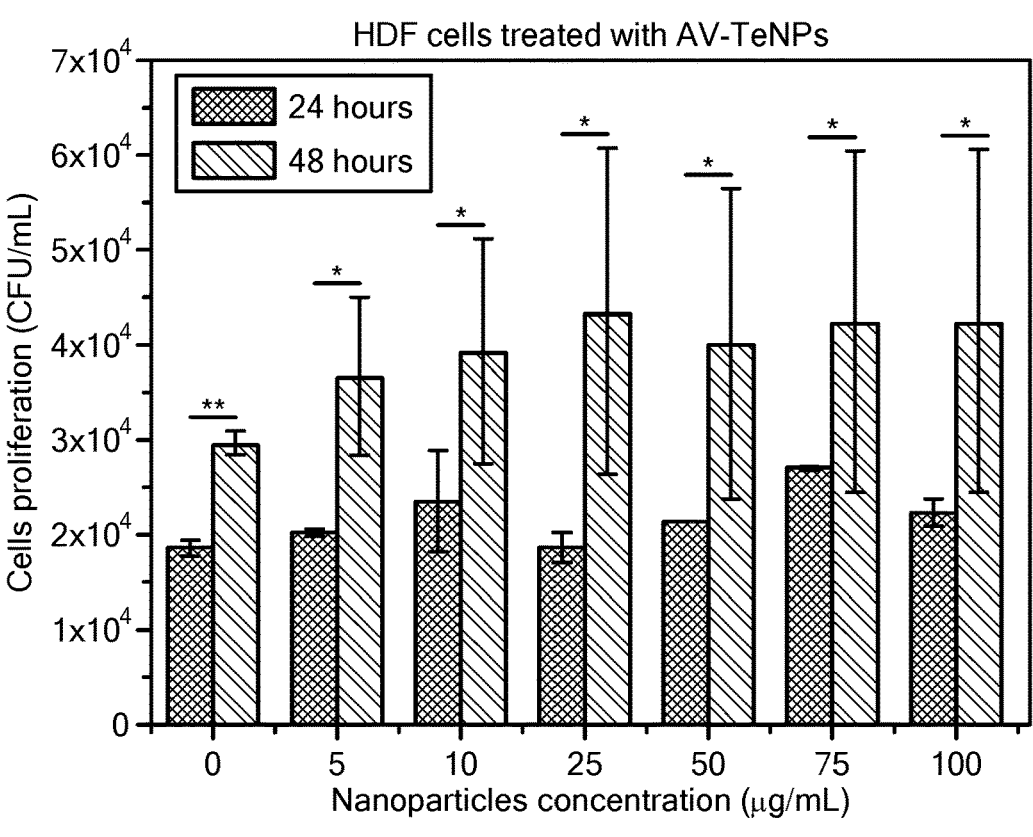
FIG. 15A shows a cytotoxicity assay with HDF cells with AV-TeNPs concentration from 0-100 μg/mL; N=3; using the same time period, p<0.005 versus control at the same time period.

A dose-relative cell proliferation decay was found when the nanosystem was cultured with HDF cells over a period of time of 24 and 48 hours (FIG. 15A). Specifically, a low cytotoxic effect was found in a range of concentrations between 5 and 50 μg/mL at 24 hours, while this effect was increased at concentrations up to 75 μg/mL at 48 hours. Therefore, the optimum working range for the AV-TeNPs, where the NPs could be considered cytocompatible, was determined to be about 5 to 50 μg/mL in experiments up to 48 hours.

Figure 15B:
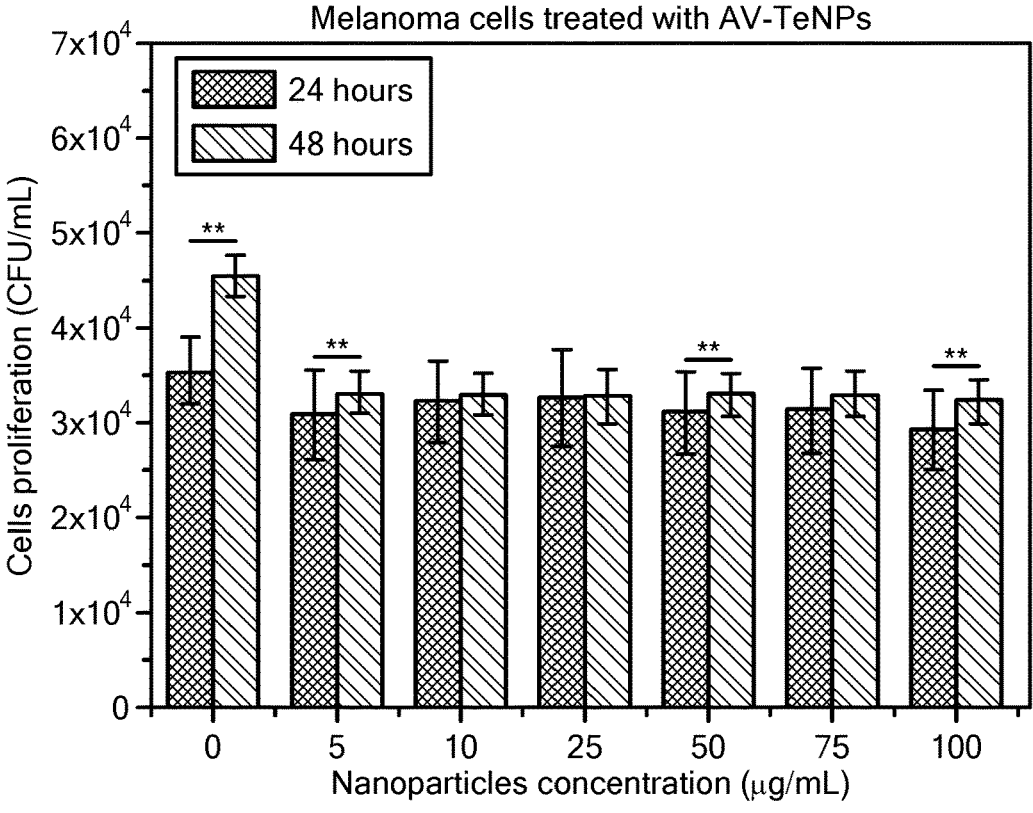
FIG. 15B shows a cytotoxicity assay with melanoma cells with AV-TeNPs concentration from 0-100 μg/mL; N=3; using the same time period, p<0.005 versus control at the same time period.

Moreover, a substantial decay in cell proliferation decay was found when the AV-TeNPs were cultured with melanoma cells over 48 hours over all the range of concentrations (FIG. 15B). The anticancer effect was found towards melanoma cells in a range of concentrations up to 50 μg/mL at 24 hours with low cytotoxic effect, while the range was increased to a concentration of 75 μg/mL at 48 hours. Therefore, the AV-TeNPs can be considered anticancer at the concentration up to 50 μg/mL for a 2-day treatment. The half maximal inhibitory concentration ($IC_{50}$) values were calculated in Table 3 to study the cytotoxic effect of the AV-TeNPs.

TABLE 3

$IC_{50}$ values (μg/mL) for the AV-TeNPs cultured with HDF and melanoma cells.

| Exposed cells | 24 hours | 48 hours |
|---|---|---|
| HDF | 74.78 | 67.70 |
| Melanoma | 1.418 | 54.06 |

These $IC_{50}$ values differ from others found in literature, showing a decrease of the $IC_{50}$ values for the AV-TeNPs. For example, Yang et al. have investigated the anticancer effect of Te nanodots synthesized using the hollow albumin nanocages, that were tested against 4T1 tumor cells with $IC_{50}$=880 μg/mL (Yang et al. 2017).

The cytotoxic effect of Te nanostructures can be the result of active physicochemical interactions of elemental Te with the functional groups of intracellular proteins and the bases and phosphate groups in DNA. Both results of the AV-TeNP cell studies (low cytotoxicity for healthy human cells and a significant delay in the growth of cancer cells) can be derived from the aloe vera itself and the compounds that remain on, surrounding or within the nanomaterial structure. The enhanced biocompatibility in AV-TeNPs (FIG. 15A) can be due to the presence of a natural, organic coating that encompasses the Te core (see FIG. 4C). The presence of a carbon layer (FIG. 6C) as the natural coating demonstrates a biodegradable material coating that can enhance cell proliferation. The XPS and EDX atomic compositions (Table 1) support a biodegradable coating including components of aloe vera extract because the FT-IR spectrum (FIG. 8) corresponds to the functional groups of the most representative phytochemical constituents found in the aloe vera extract, including polysaccharides (e.g. acemannam, galactan and pectin), proteins, vitamins, enzymes, organic acids, phenolic substances, phytosterol, flavones, organic acids and quinones (Table 2). Any biodegradable and biocompatible coating on the Te core of the AV-TeNPs can provide tellurium nanoparticles with enhanced biocompatibility, with cytological compatibility, and with anticancer and antimicrobial activity. A coating including one or more polysaccharides, starch, glycogen, proteins, or for example, a synthetically made biodegradable, non-toxic coating can achieve enhanced biocompatibility, cytological compatibility, and antimicrobial with anticancer activity. In formulations, specially engineered coatings, for example, including cell signaling, antibodies, nucleic acids, or proteins can be utilized to target the GREEN-TeNWs to specific areas, microbes, tissues, or tumors.

Figure 14:
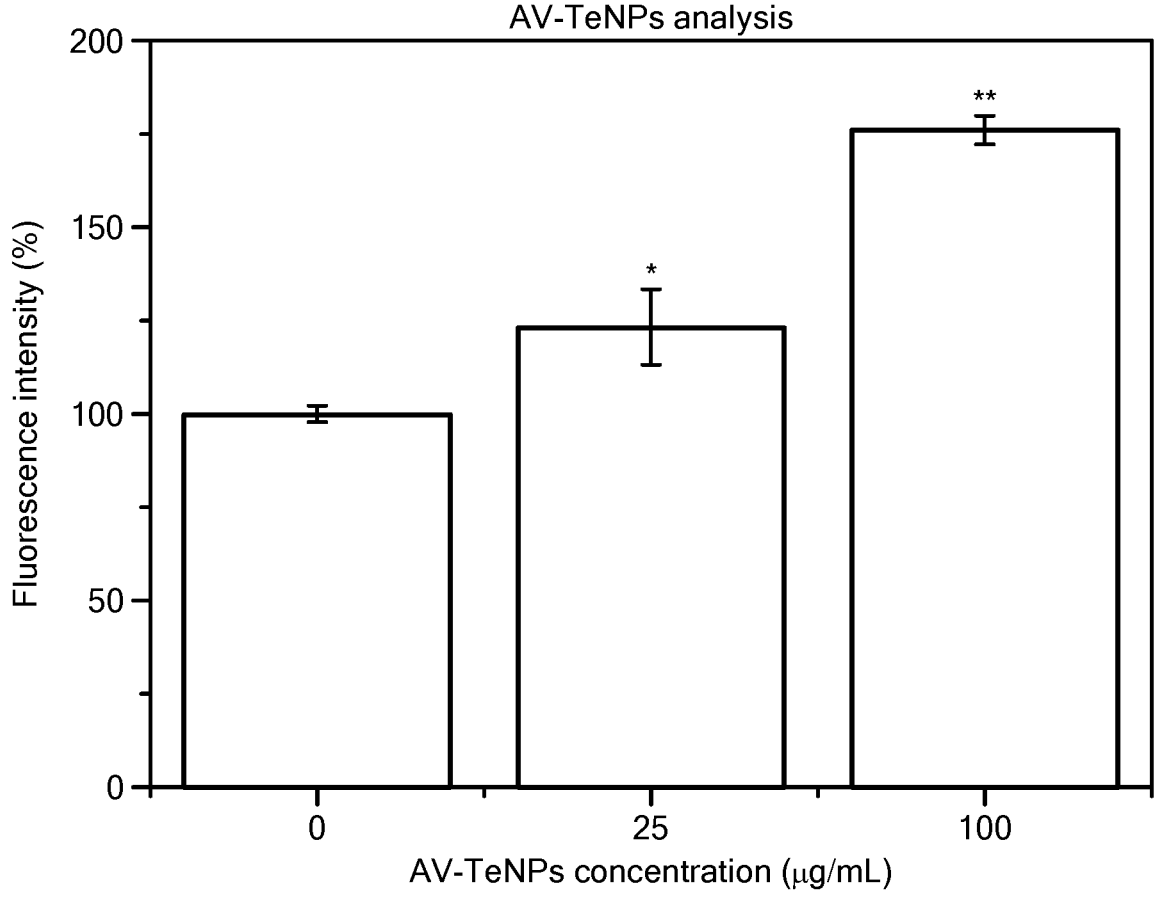
FIG. 14 shows a reactive oxygen species (ROS) study of AV-TeNPs; N=3; data is represented as mean±SD; *p<0.05, **p<0.01.

An SEM study of the interaction between human cells and the AV-TeNPs showed that HDF cells were able to successfully proliferate in the presence of the AV-TeNPs, with no apparent disruption or alteration of a membrane or healthy growth. When applied to melanoma cells, the presence of the AV-TeNPs induced a severe presence of bubbles and membrane disruption within the melanoma cell population, characteristic morphologies found on apoptotic mechanisms of cell death. As discussed previously, an increase in the NPs concentration triggers a rise in the production of ROS (FIG. 14). Therefore, this behavior might be related to the concentration of ROS within the cellular media.

The environmentally-friendly and cost-effective methods for the synthesis of tellurium (Te) nanostructures in aqueous media using aloe vera extract as a unique reducing and capping agent are shown to provide novel benefits. The AV-TeNPs can provide antibacterial coatings for medical devices or for other applications, for example, antibacterial coatings for pipes. The AV-TeNPs can provide antibacterial treatments for healthcare acquired infections (HAIs) or treatments for cancer therapeutic applications.

Tellurium NPs (AV-TeNPs) were successfully synthesized following a simple and straightforward protocol using aloe vera extract to reduce tellurite ($TeO_3^{2-}$) ions dissolved in an aqueous media to elemental tellurium ($Te^0$) in the form of NPs. Some of the biologically-active components present in the aloe vera extract are vitamins, enzymes, minerals, sugars, lignin, saponins, and several amino acids, which represent a standard composition for many other plant extracts. Sugars derived from the mucilage layer of the plant, known as mucopolysaccharides (Surjushe, Vasani, and Saple 2008; Medda et al. 2015) can be responsible for the ionic reduction (Beattie and Haverkamp 2011). The presence of a free aldehyde group or an open ketone group within the structure of the mucopolysaccharide allows them to reduce metallic ions. Once the metallic ions have been reduced, nanoparticles formed from small metallic nuclei, which tend to naturally arrange themselves via a process called "Ostwald ripening" (Gentry, Kendra, and Bezpalko 2011). Subsequent stabilization of the AV-TeNPs was hypothesized to be caused by (a) the presence and action of the same sugars that lead to the reduction (Castro et al. 2010), or (b) the work of other organic molecules, such as fatty acids (cholesterol, camp-esterol, beta-sitosterol and lupeol) (Rao and Trivedi 2006), with a high presence in the extracts (Surjushe, Vasani, and Saple 2008; Y. Zhang et al. 2018; Velez et al. 2018). It was hypothesized that the selective interaction of these organic compounds with the forming nanoparticle nuclei leads to the specific crystallographic shapes present in the nanostruc-tures.

EXAMPLES

Example 1: Materials and Methods

Bacteria

*E. coli* (strain K-12 HB101; Bio-Rad, Hercules, CA) and *Staphylococcus aureus* subsp. *aureus* Rosenbach (*S. aureus*, ATCC® 12600™) were used for the antibacterial testing, and bacterial growth was monitored by optical density and colony counting assays. The cultures were maintained on an agar plate at 4° C. For inoculum preparation, a loop of the culture was inoculated into 5 mL sterile Luria-Bertani (LB) broth in a 15 mL conical centrifuge tube and incubated at 37° C. at 200 rpm for 24 hours. Optical density of the superna-tant phase was measured using a spectrophotometer (Spec-traMax M3, Molecular Devices, Sunnyvale, CA) at 600 nm ($OD_{600}$) to estimate the number of bacterial cells per mL.
Characterization A FreeZone Plus 2.5 Liter Cascade Console Freeze Dry System was used to purify the AV-TeNP samples and obtain the final solid. For the last steps of nanoparticle purification, an Eppendorf™ Model Centrifuge 5804 R, refrigerated, with Rotor A-4-44 including adapters for 15/50 mL conical tubes, keypad, 230 V/50-60 Hz, was used for sample cen-trifugation. Characterization of the aloe vera-based tellurium nanoparticles (AV-TeNPs) was accomplished by transmis-sion electron microscopy (TEM) using a JEM-1010 trans-mission electron microscope (JEOL USA Inc., MA). To prepare samples for imaging, particles were dried on 300-mesh copper-coated carbon grids (Electron Microscopy Sci-ences, Hatfield, PA).

A SpectraMax M3 spectrophotometer (Molecular Devices, Sunnyvale, CA) was used to measure the optical density of the bacterial cultures. Growth curves and other bacterial analyses were performed in a plate reader (Spec-traMax® Paradigm® Multi-Mode Detection Platform). For samples containing the AV-TeNPs, the inductively coupled plasma mass spectrometry (ICP-MS) (VG-Elemental Plas-maQuad 2 ICP-MS Winsford U.K.) technique was used for the determination of the tellurium chemistry.
Determining the Antimicrobial Activity of AV-TeNPs Two different bacterial species were used for the bacterial assays (*E. coli* and *S. aureus*). A colony of each was resuspended in lysogeny broth (LB) media. The bacterial suspension was placed in a shaking incubator to grow overnight at 200 rpm and 37° C.

After optical density measurements at 600 nm ($OD_{600}$) were taken to determine bacterial concentration, the over-night suspension was diluted to 106 colony forming units per milliliter ($CFU mL^{-1}$). For the antimicrobial assays, different concentrations of nanoparticles were mixed with 100 µL of bacteria in LB medium and were then added to each well of a 96-well plate (Thermo Fisher Scientific, Waltham, MA). For untreated controls, bacteria were mixed with 100 µL of LB media without nanoparticles. The final volume per each well was 200 µL. Once the plate was prepared, absorbance of all samples was measured at 600 nm on an absorbance plate reader every 2 min for 24 hours. Negative controls containing only nanoparticles and medium were used to determine the absorbance caused by the nanoparticles.

The resulting bacterial growth curves were shifted to start at the origin by subtracting the initial value from the entire curve and fitted with the modified Gompertz model. To apply the Gompertz distribution to the antimicrobial assays, a parameterization of the growth model was needed. The original Gompertz equation, which describes a sigmoidal growth curve, contains mathematical parameters (a, b, c . . . ) (Equation 1) rather than parameters with biological meanings (A, µ, and λ). Therefore, it was difficult to estimate initial values for each parameter. Additionally, it was diffi-cult to calculate the 95% confidence intervals for the bio-logical parameters if they were not estimated directly in the equation, but instead had to be calculated from the math-ematical parameters. Thus, the Gompertz equation was rewritten to substitute the mathematical parameters with A, µ, and λ (Equation 2, below). This was done by deriving an expression of the biological parameters as a function of the original, mathematical parameters and then substituting them into the original formula.

The Gompertz equation, written as, $$y=a*e^{-e^{b-ct}} \quad\quad\quad \text{(Equation 1)}$$

was modified through a series of derivations to obtain the modified Gompertz equation that was used for the fitting of the curves. As can be seen, the modified Gompertz equation is defined by mathematical parameters with a biological meaning (A, µ, and λ) rather than by mathematical param-eters [40]. The equation describes a sigmoidal growth curve:

$$y = A*e^{-e^{[\frac{\mu \cdot e}{A}(\lambda-t)+1]}} \qu\quad \text{(Equation 2)}$$

Where the parameter γ is related to the number of bacteria (corresponding to the optical density reading), A is the maximal possible value of y, µ is the maximal growth rate and λ is the lag time.

The parameters A, µ and λ were estimated according to a least-squares estimation algorithm using a GRG (General-ized Reduced Gradient) nonlinear solver.

Colony counting assays were performed as follows: bac-teria were seeded in a 96-well plate and treated with different concentrations of nanoparticles for 8 hours inside an incu-bator at 37° C. Then, the 96-well plate was removed from the incubator and all the samples were diluted with PBS in a series of vials to either ×100, ×1000 or ×10000. Three drops of a 10 microliter aliquot of each dilution were then placed in a LB-Agar plate and incubated for 8 hours inside the incubator at 37° C. The resulting number of colonies formed in each plate was counted at the end of the incuba-tion.

In Vitro Cytotoxicity Assays with AV-TeNPs

Cytotoxicity assays were performed with primary human dermal fibroblast cells (Lonza, CC-2509, AMP) and melanoma cells (ATCC® CRL-1619, Manassas, VA). The cells were cultured in Dulbecco's Modified Eagle Medium (DMEM; Thermo Fisher Scientific, Waltham, MA), supplemented with 10% fetal bovine serum (FBS; ATCC® 3O2020™, American Type Culture Collection, Manassas, VA) and 1% penicillin/streptomycin (Thermo Fisher Scientific, Waltham, MA). MTS assays (CellTiter 96® Aqueous One Solution Cell Proliferation Assay, Promega, Madison, WI) were carried out to assess cytotoxicity. Cells were seeded onto tissue-culture-treated 96-well plates (Thermo Fisher Scientific, Waltham, MA) at a final concentration of 5000 cells per well in 100 μL of cell medium. After an incubation period of 24 hours at 37° C. in a humidified incubator with 5% carbon dioxide ($CO_2$), the culture medium was replaced with 100 μL of fresh cell medium containing concentrations ranging from 25 to 175 μg/mL of AV-TeNPs.

Cells were cultured for another 24 hours in same conditions, followed by washing the cells with PBS and replacing the medium with 100 μL of MTS solution (prepared using a mixing ratio of 1:5 of MTS:medium). After the addition of the solution, the 96-well plate was incubated for 4 hours to allow for a color change. Then, the absorbance was measured at 490 nm on an absorbance plate reader (Spectra-MAX M3, Molecular Devices) for cell viability after exposure to the AV-TeNP concentration. Cell viability was calculated by dividing the average absorbance obtained for each sample by the one obtained for the control sample, and then multiplied by 100. Controls containing either cells and media or just media were also included in the 96-well plate to identify the normal growth of cells without nanoparticles and determine the absorbance of the media. Cell experiments were carried out for 24 and 48 hours.

Statistical Analysis

All experiments were repeated in triplicate (N=3) to ensure reliability of results. Statistical significance was assessed using student's t-tests, with an alpha value less than 0.05 being statistically significant. Results are displayed as mean±standard deviation.

TEM analysis was done using High-Resolution Transmission Electron Microscopy coupled with Energy Dispersive X-ray spectroscopy (HR-TEM/EDX). For the analysis, one drop of the diluted sample was placed on a 200 mesh Cu grid coated with a layer of C of 20±5 μm in thickness. The dried sample was placed into a JEOL double tilt specimen holder and inserted into JEOL 2100-F TEM being operated at 200 kV. The sample was allowed to stabilize in the microscope before imaging by allowing the column pressure to reach $9.0\times10^{-6}$ Pa. The absence of formvar as grid support increases the transmission of the electron beam. Therefore, a condenser lens aperture with a diameter of 50 μm was chosen to reduce unnecessary electron interaction with the sample, employing an emission current of 119 pA. The microscope was aligned by performing JEOL's standard alignment procedures, followed by the high-resolution alignment. The images were collected by using a GATAN camera and processed with the GATAN digital micrograph software. EDX was performed using EDAX detector, accompanied by EDAX Genesis software.

For SEM analysis, an FEI Verios 460 Field Emission Scanning Electron Microscope (FE-SEM) (FEI Europe B.V., Eindhoven, Netherlands) using selective secondary/backscattered electrons detection was also used for morphological characterization. The subsequent observation was done using 10 μL of AV-TeNPs colloid that was deposited on clean silica on (Si) substrates and allowed to dry for more than 24 hours. The images were taken with 2 kV acceleration voltage and a 25 pA electron beam current. Electron dispersive X-Ray spectroscopy (EDX) was performed using an EDX detector EDAX Octane Plus (Ametek B.V., Tilburg, Netherlands) coupled to the SEM previously mentioned, for the verification of the presence of elemental Te in the structures. SEM conditions for EDX measurements were 10 kV acceleration voltage and 400 pA beam current.

A second analysis was done, in which one drop of the diluted sample was placed on a Si wafer manufactured by Monsanto electronic materials company, with a thickness of 200±20 μm and resistance of 30±10Ω. The Si wafer was then placed in an enclosed container in order for the droplet of the sample to dry overnight. The dried wafer was attached to a flat Al stub (Ted Pella) via double-sided conductive carbon tape. Both the Al stub and Si wafer were initially cleaned separately by sonication at 35 kHz. This was done while submerged in acetone, followed by ethanol, and finally two times in DI water, sonicated in each solvent for 5 minutes. The imaging and EDX were performed at 15 kV.

The X-ray diffraction pattern was recorded using a Rigaku Miniflex 600 operating with a voltage of 40 kV, a current of 15 mA, and Cu-Kα radiation (L=1.542 Å). The measurement was done at room temperature with a step width of 0.005° (2Θ) and a scan speed of 0.25°/min. The sample for the XRD analysis was prepared by drop-casting 5 mL of the AV-TeNPs colloid onto the sample holder.

For X-ray photoelectron spectroscopy (XPS) characterization, drops of a solution containing AV-TeNPs were deposited on a clean conductive copper substrate. After water evaporation, the sample was loaded in a vacuum load-lock chamber and then transferred in the ultra-high vacuum XPS system. The XPS chamber has a base pressure of $10^{-10}$ mbar and is equipped with a hemispherical electron energy Analyzer (SPECS Phoibos 100 spectrometer) and an Al Kα (1486.29 eV) X-ray source. The angle between the hemispherical analyzer and the plane of the surface was kept at 60°. Broad scan spectrum was recorded using an energy step of 0.5 eV and a pass-energy of 40 eV while specific core levels spectra (Te 3d, O 1s, and C 1s) were recorded using an energy step of 0.1 eV and a pass-energy of 20 eV. Data processing was performed with CasaXPS software (Casa software Ltd, Cheshire, UK). The absolute binding energies of the photoelectron spectra were determined by reference to the C 1s core level at 285 eV (Beamson, G.; Briggs 1993; Taylor 2007). The contributions of the Al Kα satellite lines were subtracted.

The structural analysis of the nanostructures was carried out by infrared spectroscopy using a Fourier transform infrared (FT-IR) spectrometer, Perkin Elmer 400 FT-IR/FT-NIR in attenuated total reflectance (ATR) mode. The samples for FT-IR analysis were prepared by drop casting the Te nanostructure colloids on a sample holder heated at ~50° C. The IR spectra were scanned in the range of 500 to 4000 $cm^{-1}$ with a resolution of 4 $cm^{-1}$. The spectra were normalized, and the baseline corrected using Spectrum™ software (Perkin-Elmer).

For Raman spectroscopy, one drop of sample was placed on a Si wafer manufactured by Monsato electronic materials company, with a thickness of 200±20 μm and a resistance of 30±10Ω. The Si wafer was then placed in an enclosed container in order for the droplet of the sample to dry overnight. The Si wafer was initially cleaned by sonication at 35 kHz. This was done while submerged in acetone, followed by ethanol, then DI water, and finally DI water again, sonicated in each solvent for 5 minutes. The Raman spectroscopy analysis was performed by using an EZRaman-N from Enwave Optronics, Inc. with a wavelength of 532 nm at 500 mW.

Secondary electron imaging (SEI) was performed on the Zeiss ORION NanoFab configured with a secondary ion mass spectrometer (SIMS) which enables the simultaneous detection of up to 4 atomic and small clusters species. The ORION NanoFab is a multi-ion beam platform (Ga, He, Ne) that provides high-resolution secondary electron (SE) imaging at 0.5 nm spatial resolution with a 35 keV He⁺ beam and elemental characterization at 15 nm spatial resolution with a 20 keV Ne beam. More specifically, elemental characterization was based on the mass analysis of Secondary Ions (SI) produced upon the impact of a sample with an ion beam, neon in this case. SIMS is a highly sensitive surface analytical technique that allows for the detection of all elements, including isotopes, from the periodic table. The combination of these two modalities on one instrument yielded a direct correlative SE and elemental mapping of the exact same area at high spatial resolution.

Example 2: Synthesis of AV-TeNPs

Tellurium Nanoparticle Synthesis and Purification

Precursors employed for the green synthesis of tellurium nanoparticles were sodium tellurite ($Na_2TeO_3$) (Sigma Aldrich, St. Louis, MO) and aloe vera extracts. The aloe vera leaves were purchased from a local vendor and sterilized to remove potential contaminants. For the extract preparation, 100 g of aloe vera leaves were finely cut into small pieces and boiled in a 500 mL beaker together with 100 mL of deionized water for 30 minutes. During that time, the initially clear water turned brownish. After boiling, the solution was cooled and filtered using a 0.2 μm pore size filter coupled with a vacuum. The cooled brownish leaf broth was then stored in the refrigerator at 4° C. prior to use in experiments as the unique liquid medium for the reaction.

A stock solution of 10 mM sodium tellurite was prepared in deionized water and a final concentration of 2 mM in 20 mL of deionized water was mixed with the same amount of aloe vera extract and stirred at room temperature for 15 min. The mixture was then added carefully to a 100 mL, Teflon-lined autoclave reactor (Fisher Scientific) and heated at 60° C. for 5 hours. After this time, the reactor was removed from the oven and opened. The resulting black solution was poured into a 50 mL Falcon centrifuge tube and centrifuged at 10,000 rpm for 20 min. Thereafter, a black precipitate had formed on the bottom of the container and was collected and washed twice with deionized water to remove potential additional compounds from the reaction. After both washes, the pellet was mixed and homogenized with 5 ml of deionized water and refrigerated for 4 h at –80° C. Then, the glass vial containing the frozen solution was lyophilized and left to dry overnight. The powder was then collected, weighed and dissolved in autoclaved water for further experiments.

The experiments demonstrated the ability of the aloe vera extract to reduce tellurite ($TeO_3^{2-}$) ions dissolved in the liquid medium to elemental tellurium ($Te^0$) in the form of nanoparticles, with a quick reaction rate and a facile and straightforward procedure.

While the exact mechanism of ion reduction by the aloe vera extract is not completely known, some hypotheses may be made based on the literature and the data presented herein. Active components that are present in the aloe vera extract include vitamins, enzymes, minerals, sugars, lignin, saponins and several amino acids, which represent a standard composition for many plant extracts. The sugars in the aloe vera extract, specifically, are derived from the mucilage layer of the plant, known as mucopolysaccharides [41, 42]. The effect of sugar in the ion reduction has been reported before [40]. Therefore, it is postulated that sugars present in aloe vera extract, like glucose, fructose, or polymannose, may have an influential role in the metallic reduction. The presence of a free aldehyde group or an open ketone group within the structure of the mucopolysaccharide allows them to reduce metallic ions.

Once the ions have been reduced, nanoparticles form from small metallic nuclei, which tend to naturally arrange themselves via a process called "Ostwald ripening." The Ostwald ripening principle proposes that more significant nanoparticles grow at the expense of small ones, which eventually disappear as the bigger particles grow exponentially [43]. However, this process must be controlled by the presence of a stabilizer, together with the reducing agents in the extract media. It is well known that the stability of nanoparticles in solution depends on many factors, one of the most important being the presence of a stabilizer [44]. In the case of the aloe vera extract, the stabilization may be achieved in one of two ways: (a) the presence and action of the same sugars that lead to the reduction, or (b) the work of other organic molecules, such as fatty acids cholesterol, campesterol, beta-sitosterol and lupeol, present in the aloe vera extract at a large enough concentration to have an effect [45]. The selective interaction of these organic compounds with forming nanoparticle nuclei may lead to the specific crystallographic shapes present in the nanostructures. In addition to a stabilizer, the use of a hydrothermal step in the reaction helps the nucleation of nanoparticles because the growth rate depends on temperature [46]. Moreover, pressure can also help the nucleation, accelerating the creation of nanostructures [47].

The synthesis mechanism proposed herein is far cleaner than traditional chemical synthesis methodologies that employ reducing agents as L-ascorbic acid or hydrazine, which enables fast reaction rates but introduce a safety concern when these reagents are used. For instance, hydrazine is considered a highly reactive agent, corrosive and extremely toxic. The proposed mechanism is feasible, easy, low cost, eco-friendly and quick compared to other chemical methods for the synthesis of tellurium nanostructures, allowing a potential scale-up for nanoparticle synthesis.

Example 3: Characterization of AV-TeNPs

Figure 1B:
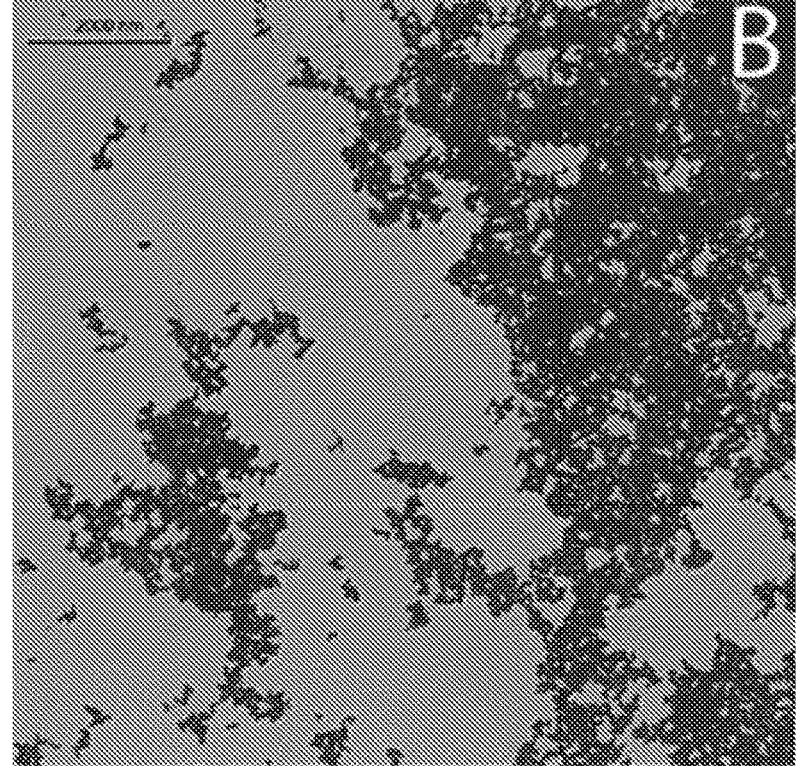
FIG. 1B shows a transmission electron microscopy (TEM) image of green-synthesized AV-TeNP clusters (aloe vera-mediated tellurium nanoparticle clusters).

The morphology and size of the AV-TeNPs were characterized using TEM. AV-TeNPs showed a uniform distribution with two different morphologies present within the solution. Significant clusters of amorphous spheres with nanorods embedded within the structures were observed in a preliminary TEM characterization right after the synthesis, with no centrifugation or wash procedure employed (FIGS. 1A and 1B). FIGS. 1A and 1B show transmission electron microscopy (TEM) images of the green-synthesized AV-TeNPs clusters. The clusters (FIGS. 1A, 1B) were easily separated once the purification was completed.

The clusters seemed to disassemble and separate after the centrifugation, wash and lyophilization steps, producing a uniform distribution of nanorods together with some amorphous nanospheres. AV-TeNPs seemed to be aggregated to the rods, usually appearing together. Moreover, prominent clusters did not occur over time, verified by the TEM measurements taken a week after the synthesis, directly from the final solution.

Nanorods with a length 100±19 nm and width of 5±2 nm tended to aggregate, forming structures with up to 10 rods together with some of the nanospheres. FIGS. 2A-2D show transmission electron microscopy (TEM) images of the tellurium structures. Tellurium nanorods formed aggregates (2A, 2B, and 2C) with different clusters of amorphous nanostructures (2D).

The potential combination of both a reducing agent and stabilizer may have acted as a shape control agent, bonding different facets of the structure with different degrees of strength. This allows different faces of the nuclei to grow faster than others, producing the elongated rods as shown in FIGS. 2A-2D. The absence of debris within the TEM images indicates that purification was accomplished successfully, eliminating by-products from the synthesis.

Energy-dispersive X-Ray Spectroscopy (EDX, FIG. 3) was used to determine the composition of the nanoparticles. Characteristic peaks for tellurium were found together with carbon and oxygen, confirming the presence of organic material surrounding the nanorods. The presence of aluminum and copper peaks was due to the composition of the sample mount employed for the measurements and the copper grids, respectively.

Example 4: Antimicrobial Activity of AV-TeNPs

Antimicrobial activity of the AV-TeNPs was tested against *E. coli* and *S. aureus* in a range of concentrations between 5 and 75 µg/mL. As seen in FIGS. 11A-11B, AV-TeNPs caused a substantial delay or inhibition in the growth of both bacteria. The inhibition is especially noticeable in the case of *E. coli*. In both bacteria, the concentration of nanoparticles does not seem to show significant differences in the pattern of inhibition. In FIGS. 4A-4B, the effect of green-synthesized AV-TeNPs on *E. coli* (4A) and *S. aureus* (4B) was measured on growth of a 106 CFU mL suspension of *E. coli* (4A) and *S. aureus* (4B) over 24 hours in the presence of different concentrations of the AV-TeNPs. The values represent the mean±standard deviation, N=3.

All the parameters in the Gompertz equation were calculated and plotted for analysis. Parameter A represents the maximum specific growth of the bacteria under experimental conditions. Upon analysis, it was found that a more significant nanoparticle concentration led to a lower asymptotic absorbance value (FIG. 12A). The maximum growth rate parameter, was also analyzed (FIG. 12B). The plots revealed that a higher AV-TeNP concentration resulted in lower maximum bacterial growth rate.

The bacterial lag-time parameter A was analyzed, and results are shown in FIG. 12C. The plot in FIG. 12C showed that a higher AV-TeNP concentration led to a shorter lag phase for bacterial growth. Since the lag phase refers to the point where bacteria are adapting to the growth conditions offered by the media, the longer lag phase seen for media with nanoparticles (compared to the control) suggests that the nanoparticle presence delays the maturing of bacteria, slowing their cell division and proliferation. The presence of nanoparticles may affect the bacterial growth cycle through the synthesis of RNA, enzymes, or other molecules involved in this phase [48]. The parameters A (5A), µ (5B) and λ (5C) were analyzed using software.

From the colony forming unit assays shown in FIGS. 13A-13B, it is possible to see that all the nanoparticles concentrations were able to cause a significant delay in the bacterial growth. This effect was especially noticeable in the experiments with *E. coli*. FIGS. 13A-13B show colony counting assays of (6A) *E. coli* and (6B) *S. aureus* after being treated for 8 hours with AV-TeNPs; N=3, *p<0.01 versus control, **p<0.005 versus control.

$IC_{50}$ values were obtained with the aim to show the minimum inhibitory concentration for each one of the bacterial tests. For *Escherichia coli* experiments, $IC_{50}$ value was 9.15±2.76 µg/mL, while for *Staphylococcus aureus* was 13.55±4.98 µg/mL. The AV-TeNPs have an enhanced antibacterial activity compared to other tellurium nanostructures reported in literature.

Antimicrobial activity of nanoparticles could be due to the production of reactive oxygen species (ROS) within the bacteria upon contact with the AV-TeNPs, although further testing is needed to confirm this hypothesis. ROS are chemically reactive agents containing oxygen within the molecules, such as hydroxyl ($OH^-$) or superoxide ($O^{2-}$) groups. Although these species usually are formed as a natural product of the metabolism of oxygen in cells, the exposure of cells to metallic nanoparticles causes a higher than normal rise in ROS concentration. It is hypothesized that the overproduction of ROS within the bacteria is caused by interaction of the bacterial membrane with tellurium ions, which are released from the nanostructures. Moreover, several organic ligands that may be present on the surface of the nanoparticles which can interact with the cell membrane, producing pits and allowing ion penetration of the membrane. These compounds, like saponin, terpenoids or flavonoids of the aloe vera may be present in different concentrations [51]. Further interactions with the membrane increase its permeability, which eventually leads to the irreversible lysis of the cells [52].

Furthermore, the observed differences in the bacterial inhibition rates can be related to the differences in morphology and structure of both bacteria species. While Gram-positive bacteria (e.g., *S. aureus*) have a thick multilayer of peptidoglycan, Gram-negative bacteria (e.g. *E. coli*) have a thin single layer of this substance, which may explain why the AV-TeNPs were more efficient at inhibiting the growth of *E. coli*. It is well known that Gram-negative bacteria show a low resistance to physical disruption [53], which further explains why the nanoparticles had a stronger effect on *E. coli* compared to *S. aureus*.

The presence of phenols and sulfur within the composition of aloe vera extract, which are highly likely to have remained within the structure of the AV-TeNPs, may explain this antiseptic effect [54].

Example 5: In Vitro Cytotoxicity of AV-TeNPs

In vitro cytotoxicity assays were performed with human dermal fibroblast (HDF) cells and melanoma cells. Both experiments were carried out for 24 and 48 hours to determine the evolution in the cell growth under the presence of nanomaterials in the cell media, and results are shown in FIGS. 15A-15B.

For HDF cells, the first-day treatment showed a decay in the cell growth up to 65%, with slight differences between different nanoparticle concentrations (FIG. 15A). During the second day, cells showed a high growth rate, which increased with higher nanoparticle concentrations. This fact might be due to the presence of natural organic compounds within the nanostructures, mitigating the potential cytotoxic effect of the AV-TeNPs. The presence of organic compounds from aloe vera extract, such as mannose-rich polysaccharides, may remain on the surface of the nanoparticles and interact with grow factor receptors presented in fibroblasts. Therefore, they can stimulate cell activity and proliferation, thereby increasing collagen synthesis after exposure [55].

Treatment of melanoma cells was also performed to evaluate the potential anticancer effect of the AV-TeNPs. Treatment with the same nanoparticle concentrations as those for HDF was carried out, and on the first day, the cell growth was consistently delayed for all concentrations compared to the control (FIG. 15B). After 48 hours, the delay was retained, with a cell concentration below that of the control for all nanoparticle concentrations. Therefore, these results indicate a successful inhibition of cancer cell growth using AV-TeNPs, suggesting that they have favorable anticancer properties. Literature showed that high concentrations of tellurium oxide nanoparticles, 160 mg/L, were highly toxic for human pulmonary alveolar epithelial and peripheral blood cell cultures [56]. Besides, tellurium-based agents were shown to disturb Oxidative Stress (OS) and intracellular redox balance in several cancer cell cultures. The oxidizing redox environment is affected by the presence of these agents, being fatal to them. Therefore, the production of reactive species is triggered, and it pass a critical redox threshold. As a consequence, apoptosis mechanisms are initiated [57]. Without being limited by any theory or mechanism of action, it is believed that both results of the AV-TeNP cell studies (low cytotoxicity for healthy human cells and a significant delay in the growth of cancer cells) can be derived from the aloe vera itself and the compounds that remain within the nanomaterial structure. Research has shown that polysaccharides present in aloe vera extract inhibit the binding of benzopyrene to primary rat hepatocytes. This prevents the formation of potentially cancer-initiating benzopyrene-DNA constructs. Furthermore, an induction of glutathione S-transferase activity, and the resulting decay in the concentration of the tumor-promoting compound, phorbol myristic acetate, has also been reported. Both of these mechanisms strongly suggest that aloe vera extract aids in cancer prevention [58, 59]. In FIGS. 15A-15B the results of the cytotoxicity assays with HDF cells (15A) and melanoma cells (15B) are with N=3, the same time period, **$p < 0.005$ versus control at the same time period.

As used herein, the term "about" and "approximately" are defined to be within 10%, 5%, 1%, or 0.5%.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expressions "consisting essentially of" or "consisting of".

REFERENCES

1. Sievert D. M., Ricks P., Edwards J. R., Schneider A., Patel J., Srinivasan A., et al. (2013). Antimicrobial-resistant pathogens associated with healthcare-associated infections: summary of data reported to the national healthcare safety network at the centers for disease control and prevention, 2009-2010. Infect. Control Hosp. Epidemiol.

2. Fleming, Alexander. On the Specific Antibacterial Properties of Penicillin and Potassium Tellurite. *J Pathol* 35.6 (1932): 831-42.

3. Wang, Edina C., and Andrew Z. Wang. "NANOPARTICLES AND THEIR APPLICATIONS IN CELL AND MOLECULAR BIOLOGY." Integrative biology: quantitative biosciences from nano to macro 6.1 (2014): 9-26.

4. Iravani S, Korbekandi H, Mirmohammadi S V, Zolfaghari B. Synthesis of silver nanoparticles: chemical, physical and biological methods. *Research in Pharmaceutical Sciences.* 2014.

5. Zhang X-F, Liu Z-G, Shen W, Gurunathan S. Silver Nanoparticles: Synthesis, Characterization, Properties, Applications, and Therapeutic Approaches. Yan B, ed. *International Journal of Molecular Sciences.* 2016; 17(9): 1534.

6. Park S, Park H H, Kim S Y, Kim S J, Woo K, Ko G. Antiviral Properties of Silver Nanoparticles on a Magnetic Hybrid Colloid. Schottel J L, ed. *Applied and Environmental Microbiology.* 2014; 80(8):2343-2350.

7. Jain S, Hirst D G, O'Sullivan J M. Gold nanoparticles as novel agents for cancer therapy. *The British Journal of Radiology.* 2012; 85(1010):101-113.

8. Arvizo R, Bhattacharya R, Mukherjee P. Gold nanoparticles: Opportunities and Challenges in Nanomedicine. *Expert opinion on drug delivery.* 2010; 7(6):753-763.

9. Cai W, Gao T, Hong H, Sun J. Applications of gold nanoparticles in cancer nanotechnology. *Nanotechnology, science and applications.* 2008.

10. Shi H, Magaye R, Castranova V, Zhao J. Titanium dioxide nanoparticles: a review of current toxicological data. *Particle and Fibre Toxicology.* 2013; 10:15.

11. Rasmussen J W, Martinez E, Louka P, Wingett D G. Zinc Oxide Nanoparticles for Selective Destruction of Tumor Cells and Potential for Drug Delivery Applications. Expert opinion on drug delivery. 2010; 7(9): 1063-1077.

12. Bharti C, Nagaich U, Pal A K, Gulati N. Mesoporous silica nanoparticles in target drug delivery system: A review. *International Journal of Pharmaceutical Investigation.* 2015; 5(3):124-133.

13. Carata E, Anna Tenuzzo B, Arno F, et al. Stress response induced by carbon nanoparticles in *Paracentrotus lividus. International Journal of Molecular and Cellular Medicine.* 2012; 1(1):30-38.

14. Medina Cruz D, Mi G, Webster T J. Synthesis and characterization of biogenic selenium nanoparticles with antimicrobial properties made by *Staphylococcus aureus,* methicillin-resistant *Staphylococcus aureus* (MRSA), *Escherichia coli,* and *Pseudomonas aeruginosa.* J Biomed Mater Res A. 2018 May; 106(5):1400-1412.

15. Jiang, Fengrui, Weiquan Cai, and Guolong Tan. "Facile Synthesis and Optical Properties of Small Selenium Nanocrystals and Nanorods." Nanoscale Research Letters 12 (2017): 401.

16. Wadhwani, Sweety A et al. "Green Synthesis of Selenium Nanoparticles Using *Acinetobacter* Sp. SW30: Optimization, Characterization and Its Anticancer Activity in Breast Cancer Cells." International Journal of Nanomedicine 12 (2017).

17. Pugin, Benoit et al. "Glutathione Reductase-Mediated Synthesis of Tellurium-Containing Nanostructures Exhibiting Antibacterial Properties." Ed. H. Nojiri. Applied and Environmental Microbiology 80.22 (2014): 7061-7070. PMC.

18. Liu, Jun et al. "Understanding the Solvent Molecules Induced Spontaneous Growth of Uncapped Tellurium Nanoparticles." Scientific Reports 6 (2016): 32631.

19. Zannoni D, Borsetti F, Harrison J J, Turner R J. The bacterial response to the chalcogen metalloids Se and Te. Adv. Microb. Physiol. 2008

20. Ba L A, Doring M, Jamier V, Jacob C. Tellurium: an element with great biological potency and potential. Organic & Biomolecular Chemistry. 2010; 8(19):4203-4216.

21. Turner R J, Weiner J H, Taylor D E. Tellurite-mediated thiol oxidation in *Escherichia coli*. Microbiology-UK. 1999; 145(9):2549-2557.

22. Ramos-Ruiz A, Wilkening J V, Field J A, Sierra-Alvarez R. Leaching of cadmium and tellurium from cadmium telluride (CdTe) thin-film solar panels under simulated landfill conditions. *Journal of hazardous materials*. 2017; 336:57-64.

23. Carotenuto G, Palomba M, De Nicola S, Ambrosone G, Coscia U. Structural and Photoconductivity Properties of Tellurium/PMMA Films. Nanoscale Research Letters. 2015; 10:313.

24. Lin S, Li W, Chen Z, Shen J, Ge B, Pei Y. Tellurium as a high-performance elemental thermoelectric. *Nature Communications*. 2016; 7:10287.

25. Turner R J, Borghese R, Zannoni D. Microbial processing of tellurium as a tool in biotechnology. Biotechnol. Adv. 2012; 30(5):954-963.

26. Washington, DC: U.S. Department of Energy; 2011. Critical materials strategy.

27. G Guisbiers et al 2017 Synthesis of tunable tellurium nanoparticles Semicond. Sci. Technol. 32 04LT0.

28. Guihua Li, Xuzhong Cui, Cuiying Tan and Nan Lin. Solvothermal synthesis of polycrystalline tellurium nanoplates and their conversion into single crystalline nanorods. RSC Adv., 2014, 4, 954-958.

29. Fernandez-Lodeiro J, Rodriguez-Gonzalez B, Novio F, et al. Synthesis and Characterization of PtTe2 Multi-Crystallite Nanoparticles using Organotellurium Nanocomposites. *Scientific Reports*. 2017; 7:9889.

30. Liu J, Liang C, Zhu X, Lin Y, Zhang H, Wu S. Understanding the Solvent Molecules Induced Spontaneous Growth of Uncapped Tellurium Nanoparticles. *Scientific Reports*. 2016; 6:32631.

31. Gomez-Graria S, Perez-Ameneiro M, Vecino X, et al. Biogenic Synthesis of Metal Nanoparticles Using a Biosurfactant Extracted from Corn and Their Antimicrobial Properties. Fang J (James), Nann T, eds. *Nanomaterials*. 2017; 7(6):139.

32. Qingyi Lu, Feng Gao, and, and Sridhar Komarneni. A Green Chemical Approach to the Synthesis of Tellurium Nanowires. Langmuir 2005 21 (13), 6002-6005.

33. Iravani S. Bacteria in Nanoparticle Synthesis: Current Status and Future Prospects. *International Scholarly Research Notices*. 2014; 2014:359316.

34. Ollivier P R L, Bahrou A S, Marcus S, Cox T, Church™, Hanson T E. Volatilization and Precipitation of Tellurium by Aerobic, Tellurite-Resistant Marine Microbes. *Applied and Environmental Microbiology*. 2008; 74(23):7163-7173.

35. Tippayawat P, Phromviyo N, Boueroy P, Chompoosor A. Green synthesis of silver nanoparticles in aloe vera plant extract prepared by a hydrothermal method and their synergistic antibacterial activity. Corbo M R, ed. PeerJ. 2016; 4: e2589.

36. Yadav J P, Kumar S, Budhwar L, Yadav A, Yadav M (2016) Characterization and Antibacterial Activity of Synthesized Silver and Iron Nanoparticles using Aloe vera. J Nanomed Nanotechnol 7:384.

37. Chandran S P, Chaudhary M, Pasricha R, Ahmad A, Sastry M. 2006. Synthesis of goldnanotriangles and silver nanoparticles using Aloevera plant extract. Biotechnology Progress 22:577-583.

38. Reynolds T, Dweck A. 1999. Aloe vera leaf gel: a review update. Journal of Ethnopharma-cology 68:3-37.

39. Emaga T H, Robert C, Ronkart S N, Wathelet B, Paquot M. 2008. Dietary fibre components and pectin chemical features of peels during ripening in banana and plantain-varieties. Bioresource Technology 99:4346-4354.

40. Gupta, Vinay K., and Seema Malhotra. "Pharmacological Attribute of Aloe Vera: Revalidation through Experimental and Clinical Studies." Ayu 33.2 (2012): 193-196.

41. Hashemi, Seyyed Abbas, Seyyed Abdollah Madani, and Saied Abediankenari. "The Review on Properties of Aloe Vera in Healing of Cutaneous Wounds." BioMed Research International 2015 (2015): 714216.

42. Nejatzadeh-Barandozi, Fatemeh. "Antibacterial Activities and Antioxidant Capacity of Aloe Vera." Organic and Medicinal Chemistry Letters 3 (2013): 5.

43. De Jong, Wim H, and Paul J A Borm. "Drug Delivery and Nanoparticles: Applications and Hazards." International Journal of Nanomedicine 3.2 (2008): 133-149.

44. Dykman, L. A., and N. G. Khlebtsov. "Gold Nanoparticles in Biology and Medicine: Recent Advances and Prospects." Acta Naturae 3.2 (2011): 34-55.

45. Logaranjan, Kaliyaperumal et al. "Shape- and Size-Controlled Synthesis of Silver Nanoparticles Using Aloe Vera Plant Extract and Their Antimicrobial Activity." Nanoscale Research Letters 11 (2016): 520.

46. Kugnieruk, Sylwia et al. "Influence of Hydrothermal Synthesis Parameters on the Properties of Hydroxyapatite Nanoparticles." Ed. Horst Hahn. Beilstein Journal of Nanotechnology 7 (2016): 1586-1601.

47. Ali, Attarad et al. "Synthesis, Characterization, Applications, and Challenges of Iron Oxide Nanoparticles." Nanotechnology, Science and Applications 9 (2016): 49-67.

48. Wang, Linlin, Chen Hu, and Longquan Shao. "The Antimicrobial Activity of Nanoparticles: Present Situation and Prospects for the Future." International Journal of Nanomedicine 12 (2017): 1227-1249.

49. Zare B, Faramarzi M A, Sepehrizadeh Z, Shakibaie M, Rezaie S, Shahverdi A R. Biosynthesis and recovery of rod-shaped tellurium nanoparticles and their bactericidal activities. Mater Res Bull. 2012; 47(11):3719-3725.

50. Mojtaba Shakibaie, Mahboubeh Adeli-Sardou, Tayebe Mohammadi-Khorsand, Mandie ZeydabadiNejad, Ehsan Amirafzali, Sahar Amirpour-Rostami, Atefeh Ameri, Hamid Forootanfar. Antimicrobial and Antioxidant Activity of the Biologically Synthesized Tellurium Nanorods; A Preliminary In vitro Study. Iranian J Biotech. 2017 October; 15(4):e1580.

51. Athiban, Prakash P et al. "Evaluation of Antimicrobial Efficacy of Aloe Vera and Its Effectiveness in Decontaminating Gutta Percha Cones." Journal of Conservative Dentistry JCD 15.3 (2012): 246-248.

52. Wang, Edina C., and Andrew Z. Wang. "NANOPARTICLES AND THEIR APPLICATIONS IN CELL AND MOLECULAR BIOLOGY." Integrative biology: quantitative biosciences from nano to macro 6.1 (2014): 9-26.

53. Farkas, Attila et al. "Comparative Analysis of the Bacterial Membrane Disruption Effect of Two Natural Plant Antimicrobial Peptides." Frontiers in Microbiology 8 (2017): 51.

54. Banu, Asima, BC Sathyanarayana, and Goura Chattannavar. "Efficacy of Fresh Aloe Vera Gel against Multi-Drug Resistant Bacteria in Infected Leg Ulcers." The Australasian Medical Journal 5.6 (2012): 305-309.

55. Rahmani, Arshad H. et al. "Aloe Vera: Potential Candidate in Health Management via Modulation of Biological Activities." Pharmacognosy Reviews 9.18 (2015): 120-126.

56. Jamier V, Ba L A, Jacob C. Selenium- and tellurium containing multifunctional redox agents as biochemical redox modulators with selective cytotoxicity. Chem A Eur J 2010; 16: 10920-10928.

57. Nursah Aydin, Mehmet Enes Arslan, Erdal Sonmez Sonmez, Hasan Turkez. Cytotoxicity analysis of tellurium dioxide nanoparticles on cultured human pulmonary alveolar epithelial and peripheral blood cell cultures. Biomedical Research 2017; 28 (7): 3300-3304.

58. Kocik, Janusz et al. "Feeding Mice with Aloe Vera Gel Diminishes L-1 Sarcoma-Induced Early Neovascular Response and Tumor Growth." Central-European Journal of Immunology 39.1 (2014): 14-18.

59. Radha, Maharjan H., and Nampoothiri P. Laxmipriya. "Evaluation of Biological Properties and Clinical Effectiveness of Aloe Vera: A Systematic Review." Journal of Traditional and Complementary Medicine 5.1 (2015): 21-26.

The invention claimed is:

1. A method of producing coated tellurium nanostructures, the method comprising:
   a) mixing an alkali metal tellurite salt with an aqueous extract of aloe vera to obtain a suspension comprising sodium tellurite, aloe vera, and water; and
   b) heating the mixture in a sealed reaction vessel to a temperature of about 80° C. for a time from about 3 hours to about 8 hours;
   whereby coated tellurium nanostructures are produced;
   wherein the coated tellurium nanostructures resulting from step (b) comprise nanoparticles, nanorods, or a mixture thereof;
   wherein the coated tellurium nanostructures each comprise (i) a core comprising amorphous tellurium and (ii) a coating derived from material of the aloe vera extract, the coating having an average thickness of at least about 1 nm; and
   wherein the coated tellurium nanostructures are capable of inhibiting the proliferation of cancer cells without significantly inhibiting the proliferation of normal cells.

2. The method of claim 1, further comprising:
   (c) centrifuging the product resulting from step (b) to obtain a pellet;
   (d) resuspending the pellet in water; and
   (e) lyophilizing the resuspended pellet.

3. The method of claim 1, wherein in step (b) heating is performed for about 4 hours to about 7 hours.

4. The method of claim 1, wherein the alkali metal tellurite salt is selected from the group consisting of sodium tellurite, lithium tellurite, potassium tellurite, rubidium tellurite, cesium tellurite, and francium tellurite.

5. The method of claim 1, wherein the aqueous aloe vera extract is obtained by boiling diced aloe vera leaves in water for about 30 minutes.

6. A method of inhibiting proliferation of bacteria, the method comprising contacting the bacteria with the coated tellurium nanostructures made by the method of claim 1.

7. A method of inhibiting proliferation of a cancer cell, the method comprising contacting the cancer cell with the coated tellurium nanostructures made by the method of claim 1, wherein the coated tellurium nanostructures comprise (i) a core comprising amorphous tellurium and (ii) a coating comprising material derived from an aloe vera extract, the coating having an average thickness of at least 1 nm.

* * * * *